United States Patent [19]

Smith

[11] Patent Number: 4,496,742

[45] Date of Patent: * Jan. 29, 1985

[54] ANALOGS OF 5,6-DIHYDRO PGI$_2$

[75] Inventor: Herman W. Smith, Kalamazoo, Mich.

[73] Assignee: The Upjohn Company, Kalamazoo, Mich.

[*] Notice: The portion of the term of this patent subsequent to Oct. 13, 1998 has been disclaimed.

[21] Appl. No.: 426,231

[22] Filed: Oct. 4, 1982

Related U.S. Application Data

[63] Continuation-in-part of Ser. No. 310,003, Oct. 13, 1981, abandoned, which is a continuation-in-part of Ser. No. 159,738, Jun. 16, 1980, Pat. No. 4,294,759, which is a continuation-in-part of Ser. No. 94,572, Nov. 15, 1979, abandoned.

[51] Int. Cl.$^3$ .............................................. C07D 209/52
[52] U.S. Cl. ................................... 548/516; 548/509; 548/494; 548/510; 548/252; 548/253; 548/254; 548/452; 548/467
[58] Field of Search .............. 548/516, 252, 253, 254, 548/467, 452; 542/421, 426, 429, 430

[56] References Cited

U.S. PATENT DOCUMENTS 4,294,759 10/1981 Smith ................................... 548/516

Primary Examiner—Henry R. Jiles
Assistant Examiner—Bernard I. Dentz
Attorney, Agent, or Firm—L. Ruth Hattan

[57] ABSTRACT

Novel structural analogues of 5,6-dihydro PGI$_2$ of the formula:

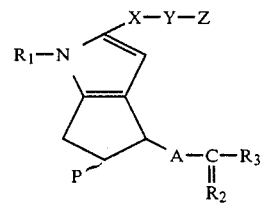

and the corresponding 10,11-didehydro-11-deoxy derivatives are useful as antiallergy agents.

10 Claims, No Drawings

ANALOGS OF 5,6-DIHYDRO PGI$_2$

Cross Reference to Related Applications

This application is a continuation-in-part of copending U.S. application Ser. No. 310,003, filed Oct. 13, 1981, now abandoned, which is a continuation-in-part of copending U.S. application Ser. No. 159,738, filed June 16, 1980 now U.S. Pat. No. 4,294,759 issued Oct. 13, 1981, which is a continuation-in-part of U.S. application Ser. No. 094,572, filed Nov. 15, 1979, now abandoned.

FIELD OF THE INVENTION

This invention relates to novel structural analogs of 5,6-dihydroprostacyclin (PGI$_1$) and to the use of those compounds as antiasthma compounds.

Prostacyclin is an endogenously produced compound in mammalian species, being structurally and biosynthetically related to the prostaglandins (PG's). The 5,6-dihydro- compound does not have a double bond between the 5 and 6 positions.

PRIOR ART

Nicolaou, et al, discloses in J. Am. Chem. Soc. 101 (3), 766 (1979) 6,9-pyridazaprostacyclin and its derivatives, the dihydropyridazaprostacyclin and N-oxides. U.S. Pat. No. 4,112,224 discloses bicyclic nitrogen containing compounds which are analogues of the prostaglandins. U.S. Pat. No. 4,097,489 discloses 9-deoxy-9α,6-nitrilo or 6,9α-imino-PGF compounds.

Compounds of the following general formula are claimed in copending U.S. application Ser. No. 159,738, filed June 16, 1980 now U.S. Pat. No. 4,294,759 issued Oct. 13, 1981.

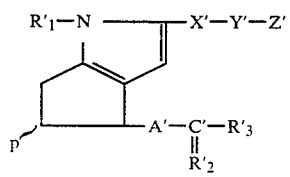

Formula A wherein Z' is (a) —CO$_2$R'$_8$ wherein R'$_8$ is a pharmaceutically acceptable metal or amine cation, hydrogen, a straight or branched alkyl group having from 1 to 6 carbon atoms, phenyl, phenyl substituted in any position with from 1 to 3 substituents selected from chlorine or a straight or branched alkyl group having from 1 to 3 carbon atoms, or phenyl substituted in the para-position with —NHCOR'$_{10}$, —COR'$_{11}$, —OCOR'$_{12}$, or —CH=NNHCONH$_2$ wherein R'$_{10}$ is methyl, phenyl, acetamidophenyl, benzamidophenyl, or amino; R'$_{11}$ is methyl, methoxy, phenyl or amino; and R'$_{12}$ is phenyl or acetamidophenyl;

(b) —CONR'$_{13}$R'$_{14}$ wherein each of R'$_{13}$ and R'$_{14}$ is the same or different and is hydrogen, an alkyl group having from 1 to 6 carbon atoms, phenyl or benzyl; or (c) —CH$_2$OR'$_5$ wherein R'$_5$ is hydrogen, a straight or branched alkyl group having from 1 to 6 carbon atoms, benzoyl, or acetyl;

wherein Y' is —CH$_2$CH$_2$—; or trans-CH=CH—; or —CH$_2$CF$_2$;

wherein X' is —(CH$_2$)$_n$— and n is 2 or 4;

wherein R'$_1$ is hydrogen, a straight or branched alkyl group having from 1 to 4 carbon atoms, a cycloalkyl group having from 3 to 7 carbon atoms or

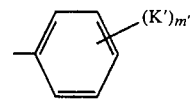

wherein K' is a straight or branched alkyl group having from 1 to 3 carbon atoms, fluorine, chlorine, trifluoromethyl, methoxy, phenyl, —CO$_2$R'$_8$ wherein R'$_8$ has the meaning defined hereinabove, or —CH$_2$OR'$_{19}$ wherein R'$_{19}$ is hydrogen, a straight or branched alkyl group having from 1 to 6 carbon atoms, acetyl or benzoyl; and m' is zero to 3 with the proviso that m' is 1 when K' is —CO$_2$R'$_8$, —CH$_2$OR'$_{19}$ or phenyl;

wherein P' is hydrogen, hydroxy or hydroxymethyl, i.e., —CH$_2$OH;

wherein A' is —CH$_2$CH$_2$—, cis- or trans-CH=CH; or —C≡C—;

wherein R'$_2$ is H,H; =O; α—R'$_4$,β—OR'$_{25}$; or α—OR'$_{25}$,β—R'$_4$ wherein R'$_4$ is hydrogen or an alkyl group having from 1 to 3 carbon atoms, and R'$_{25}$ is hydrogen, methyl, or acetyl; and wherein R'$_3$ is cis-2-pentenyl, —C(R'$_6$)(R'$_7$)—B'—E' or —C(R'$_6$)(R'$_7$)C$_q$'H$_{2q}$'—CH$_3$ wherein B' is a bond, oxa, or an alkylene moiety having from 1 to 6 carbon atoms; E' is

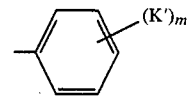

wherein each of K' and m' has the meaning defined hereinabove; q' is 1 to 4; and each of R'$_6$ and R'$_7$ is hydrogen, fluorine or an alkyl group having from 1 to 4 carbon atoms with the provisos that when R'$_6$ is fluorine, R'$_7$ is either hydrogen or fluorine, and when B' is oxa, each of R'$_6$ and R'$_7$ is other than fluorine; and pharmaceutically acceptable salts thereof.

European patent application No. 29341 corresponding to aforementioned U.S. application Ser. No. 159,738 now U.S. Pat. No. 4,294,759 issued Oct. 13, 1981 was published on May 27, 1981.

SUMMARY OF THE INVENTION

This invention provides compounds of Formulas I and II below:

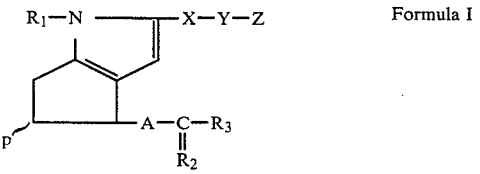

Formula I

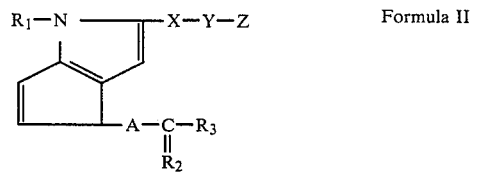

Formula II

The present invention provides compounds of Formulas I and II wherein the various substituent groups Z, Y, X, $R_1$, A, $R_2$ and $R_3$ and P in the case of Formula I have the meanings defined hereinbelow:

wherein Z is
- (a) $-CO_2R_8$ wherein $R_8$ is a pharmaceutically acceptable metal cation, hydrogen, a straight or branched alkyl group having from 1 to 6 carbon atoms, phenyl, phenyl substituted in any position with from 1 to 3 substituents selected from chlorine or a straight or branched alkyl group having from 1 to 3 carbon atoms, or phenyl substituted in the para-position with $-NHCOR_{10}$, $-COR_{11}$, $-OCOR_{12}$, or $-CH=NNHCONH_2$ wherein $R_{10}$ is methyl, phenyl, acetamidophenyl, benzamidophenyl, or amino; $R_{11}$ is methyl, methoxy, phenyl or amino; and $R_{12}$ is phenyl or acetamidophenyl;
- (b) $-CONR_{13}R_{14}$ wherein each of $R_{13}$ and $R_{14}$ is the same or different and is hydrogen, an alkyl group having from 1 to 8 carbon atoms, phenyl or benzyl;
- (c) $-CH_2OR_5$ wherein $R_5$ is hydrogen, a straight or branched alkyl group having from 1 to 6 carbon atoms, benzoyl, a straight or branched alkanoyl group having from 2 to 5 carbon atoms, tetrahydropyranyl, trimethylsilyl, tert-butyldimethylsilyl, or

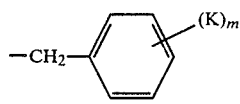

wherein K is a straight or branched alkyl group having from 1 to 6 carbon atoms, fluorine, chlorine, bromine, trifluoromethyl, a straight or branched alkoxy group having from 1 to 4 carbon atoms, phenyl, an alkanoyl group having from 2 to 5 carbon atoms, an alkanoylamido group having from 2 to 5 carbon atoms, nitro, or
- (i) $-CO_2R_8$ wherein $R_8$ has the meaning defined hereinabove;
- (ii) $-CH_2OR_{19}$, $-OR_{19}$, or $-SR_{19}$ wherein $R_{19}$ is hydrogen, a straight or branched alkyl group having from 1 to 6 carbon atoms, an alkanoyl group having from 2 to 5 carbon atoms, benzoyl, benzyl, trimethylsilyl, tert-butyldimethylsilyl or tetrahydropyranyl; or
- (iii) $-NR_{20}R_{21}$ wherein each of $R_{20}$ and $R_{21}$ is the same or different and is hydrogen or an alkyl group having from 1 to 6 carbon atoms;

and m is zero to 3 with the provisos that when K is phenyl, $-CO_2R_8$ or $-CH_2OR_{19}$, m is 1, and when K is $-OR_{19}$ or $-SR_{19}$, m is 1 or 2;

(d) 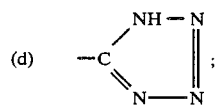

wherein Y is $-CH_2CH_2-$, cis- or trans-$CH=CH-$, or $-CH_2CF_2$;
wherein X is $-(CH_2)_n$ wherein n is 1 to 5;
wherein $R_1$ is hydrogen, a straight or branched alkyl group having from 1 to 6 carbon atoms, a cycloalkyl group having from 3 to 7 carbon atoms, a bicycloalkyl group having from 6 to 10 carbon atoms, or

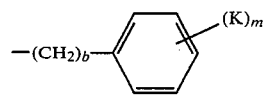

wherein b is zero or 1, and each of K and m has the meaning defined hereinabove;
wherein P is hydrogen, $\sim OR_5$ or $\sim CH_2OR_5$ wherein $R_5$ has the meaning defined hereinabove;
wherein A is $-CH_2CH_2-$, cis- or trans-$CH=CH-$ or $-C\equiv C-$;
wherein $R_2$ is H,H; $=O$; $\alpha-R_4,\beta-OR_5$; or $\alpha-OR_5,\beta-R_4$ wherein $R_4$ is hydrogen or an alkyl group having from 1 to 4 carbon atoms, and $R_5$ has the meaning defined hereinabove; and
wherein $R_3$ is cis-2-pentenyl, $-C(R_6)(R_7)-B-E$ or $-C(R_6)(R_7)C_qH_{2q}-CH_3$ wherein B is a bond, oxa, or an alkylene moiety having from 1 to 6 carbon atoms; E is

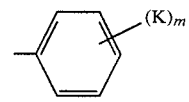

wherein each of K and m has the meaning defined hereinabove; q is 1 to 4; and each of $R_6$ and $R_7$ is hydrogen, fluorine or an alkyl group having from 1 to 4 carbon atoms with the provisos that when $R_6$ is fluorine, $R_7$ is either hydrogen or fluorine, and when B is oxa, each of $R_6$ and $R_7$ is other than fluorine; and pharmaceutically acceptable salts thereof, with the further overall proviso that in the compounds of Formula I when in each occurrence of $R_5$ it is hydrogen, a straight or branched alkyl group having from 1 to 6 carbon atoms, benzoyl or an alkanoyl group having 2 carbon atoms, and when in each occurrence of K it is a straight or branched alkyl group having from 1 to 3 carbon atoms, fluorine, chlorine, trifluoromethyl, an alkoxy group having 1 carbon atom, phenyl, $-CO_2R_8$ wherein $R_8$ has the meaning defined hereinabove, or $-CH_2OR_{19}$ wherein $R_{19}$ is hydrogen, a straight or branched alkyl group having from 1 to 6 carbon atoms, an alkanoyl group having 2 carbon atoms, or benzoyl, and when Z is other than

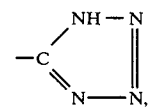

and when $R_1$ is other than a bicycloalkyl group having from 6 to 10 carbon atoms or a straight or branched alkyl group having 5 or 6 carbon atoms, and when Y is other than cis-$CH=CH-$, and when b is zero, n is other than 2 or 4.

The compounds of Formulas I and II wherein $R_5$ is other than tetrahydropyranyl, trimethylsilyl or tert-butyldimethylsilyl are useful as anti-asthmatic agents as described more fully hereinbelow. Also, the compounds of Formulas I and II wherein R is other than tetrahydropyranyl, trimethylsilyl, or tert-butyldimethylsilyl excepting 6,9-deepoxy-6,9-[[o-(methylthio)phenyl-]imino]-$\Delta^{6,8}$-prostaglandin $I_1$, methyl ester are inhibitors of 5-lipoxygenase rendering said compounds useful in the treatment of inflammation. The compounds of Formulas I and II wherein $R_5$ is tetrahydropyranyl, trimethylsilyl or tert-butyldimethylsilyl as well as those compounds wherein $R_5$ is benzoyl having from 2 to 5 carbon atoms represent protected forms of compounds useful as intermediates in obtaining pharmaceutically useful compounds of Formulas I and II. Additionally, the compounds of Formula II are useful as intermediates in the preparation of compounds of Formula I wherein P is hydrogen.

DETAILED DESCRIPTION OF INVENTION

For purposes of convenience the compounds of Formula I of this invention may be defined as a compound wherein the various substituent groups Z, Y, X, $R_1$, P, A, $R_2$ and $R_3$ have the meanings defined hereinabove with the proviso that each compound is other than one formed when the substituent groups Z, Y, X, $R_1$, P, $R_2$ and $R_3$ have the following meanings:
wherein Z is
(a) —$CO_2R_8$ wherein $R_8$ is a pharmaceutically acceptable metal or amine cation, hydrogen, a straight or branched alkyl group having from 1 to 6 carbon atoms, phenyl, phenyl substituted in any position with from 1 to 3 substitutents selected from chlorine or a straight or branched alkyl group having from 1 to 3 substituents selected from chlorine or a straight or branched alkyl group having from 1 to 3 carbon atoms, or phenyl substituted in the para-position with —$NHCOR_{10}$, —$COR_{11}$, —$OCOR_{12}$, or —CH=$NNHCONH_2$ wherein $R_{10}$ is methyl, phenyl, acetamidophenyl, benzamidophenyl, or amino; $R_{11}$ is methyl, methoxy, phenyl or amino; and $R_{12}$ is phenyl or acetamidophenyl;
(b) —$CONR_{13}R_{14}$ wherein each of $R_{13}$ and $R_{14}$ is the same or different and is hydrogen, an alkyl group having from 1 to 6 carbon atoms, phenyl or benzyl;
(c) —$CH_2OR_5$ wherein $R_5$ is hydrogen, a straight or branched alkyl group having from 1 to 6 carbon atoms, benzoyl or an alkanoyl group having 2 carbon atoms; wherein Y is —$CH_2CH_2$—, trans-CH=CH—, or —$CH_2CF_2$—;
wherein X is —$(CH_2)_n$ and n is 2 or 4;
wherein $R_1$ is hydrogen, a straight or branched alkyl group having from 1 to 4 carbon atoms, a cycloalkyl group having from 3 to 7 carbon atoms or

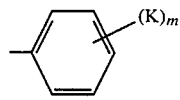

wherein K is a straight or branched alkyl group having from 1 to 3 carbon atoms, fluorine, chlorine, trifluoromethyl, and alkoxy group having 1 carbon atom, phenyl, —$CO_2R_8$ wherein $R_8$ has the meaning defined hereinabove, or —$CH_2OR_{19}$ is hydrogen, a straight or branched alkyl group having from 1 to 6 carbon atoms, an alkanoyl group having 2 carbon atoms, or benzoyl; and m is zero to 3 with the proviso that m is 1 when K is —$CO_2R_8$, —$CH_2OR_{19}$ or phenyl;
wherein P is hydrogen, ~$OR_5$ or ~$CH_2OR_5$ and each $R_5$ is hydrogen;
wherein $R_2$ is H,H; =O; $\alpha$—$R_4,\beta$—$OR_5$; or $\alpha$—$OR_5$,$\beta$—$R_4$ wherein each $R_4$ is hydrogen or an alkyl group having from 1 to 3 carbon atoms, and each $R_5$ is hydrogen, an alkyl group having 1 carbon atom, or an alkanoyl group having 2 carbon atoms; and
wherein $R_3$ has the meaning defined in Formula I except that K as used therein has the following meaning: a straight or branched alkyl group having from 1 to 3 carbon atoms, fluorine, chlorine, trifluoromethyl, an alkoxy group having 1 carbon atom, phenyl, —$CO_2R_8$ wherein $R_8$ has the meaning defined hereinabove, or —$CH_2OR_{19}$ wherein $R_{19}$ is hydrogen, a straight or branched alkyl group having from 1 to 6 carbon atoms, an alkanoyl group having 2 carbon atoms, or benzoyl.

Illustrative examples of a straight or branched alkyl group having from 1 to 6 carbon atoms are methyl, ethyl, propyl, butyl, pentyl, hexyl, isopropyl, tertbutyl, neopentyl and 2,3-dimethylbutyl. An alkyl group of a lesser carbon number is similarly interperted.

As used herein the term cycloalkyl of three to seven carbon atoms, means cyclopropyl, cyclobutyl, cyclopentyl, cyclohexyl and cycloheptyl.

The term pharmaceutically acceptable metal cations includes cations of an alkali metal such as sodium and potassium, or alkaline earth metals such as calcium and magnesium, and other acceptable metals such as aluminum.

As used herein the term alkylene moiety having from 1 to 6 carbon atoms means the group —$(CH_2)_{1-6}$—, for example, methylene, ethylene, propylene, butylene and so on.

Illustrative examples of bicycloalkyl groups having from 6 to 10 carbon atoms are bicyclo[5.1.0]octane, spiro[2.6]nonane, bicyclo[6.1.0]nonane, spiro[3.5]nonane, bicyclo[3.3.0]octane, indene, bicyclo[3.2.1]octane, spiro[4.5]decane, bicyclo[2.2.0]hexane, bicyclo[2.1.1]hexane, norbornane, and bicyclo[3.1.1]heptane.

Illustrative examples of a straight or branched alkoxy group having from 1 to 4 carbon atoms are methoxy, ethoxy, n-propoxy, isopropoxy, n-butyl and tert-butyl.

The term oxa as used herein means the moiety —O—.

The term cis-2-pentenyl as used herein means the moiety:

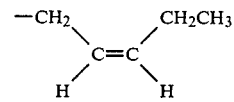

The term acetamidophenyl means the group:

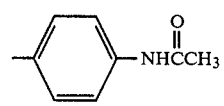

The term alkanoylamido having from 2 to 5 carbon atoms means the group:

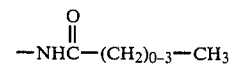

The term alkanoyl group having from 2 to 5 carbon atoms means the group:

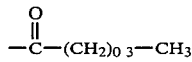

Pharmaceutically acceptable salts of the compounds of Formulas I and II are also included within the scope of the present invention. Illustrative of such salts are pharmacologically acceptable amine salts, i.e., amines which are accepted by mammals in an essentially non-toxic manner when administered to mammals in conjunction with the acid moiety of the invention. Illustrative of the amines are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about 18 carbon atoms as well as heterocyclic amines, e.g., piperidine, morpholine, pyrrolidine, piperazine, and lower-alkyl derivatives thereof, e.g., 1-methylpiperdine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, triethanolamine, ethyldiethanolamine, N-butylethanolamine, 2-amino-1-butanol, 2-amino-1-ethyl-1,3-propanediol, 2-amino-2-methyl-1-propanol, tri(hydroxymethyl)aminoethane, N-phenylethanolamine, N-(p-tert-amylphenyl)diethanolamine, galactamine, N-methylglucamine, N-methylglucosamine, ephedrine, phenylephrine, epinephrine, or procaine.

Also included within the scope of this invention are acid addition salts of the compounds of Formulas I and II which contain basic moieties capable of forming such salts. Illustrative of appropriate and useful acid addition salts are those of any suitable inorganic or organic acid. Suitable inorganic acids are, for example, hydrochloric, hydrobromic, sulfuric and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, and mandelic acid, sulfonic acids, such as methanesulfonic, ethanesulfonic and β-hydroxyethanesulfonic acid.

Examples of phenyl esters substituted in the para-position include -acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzylphenyl ester, p-amidocarbonylphenyl ester, p-methoxycarbonylphenyl ester, p-benzoyloxyphenyl ester and p-(p-acetamidobenzoyloxy)phenyl ester.

A preferred embodiment of this invention is compounds of Formula I wherein $R_1$ is a cycloalkyl group having from 6 to 10 carbon atoms or wherein $R_1$ is the group

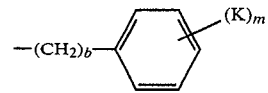

wherein b, K and m have the meanings defined hereinabove, and more preferred are those compounds wherein b is zero or wherein m is zero to 2.

Particularly preferred are compounds of Formula I wherein $R_1$ is

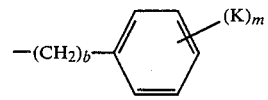

wherein b is zero and K is bromine, a straight or branched alkoxy group of from 2 to 4 carbon atoms, hydroxy, i.e., compounds wherein K is $-OR_{19}$ and $R_{19}$ is hydrogen, $-SR_{19}$, or $-NR_{20}R_{21}$ wherein each of $R_{20}$ and $R_{21}$ is hydrogen, and m is zero to 2.

Other preferred embodiments of the invention are the compounds of Formula I wherein:

P is α—$OR_5$ wherein $R_5$ is hydrogen;

A is trans-CH=CH—;

$R_2$ is α—$OR_5$,β—$R_4$ wherein $R_5$ is hydrogen or methyl and $R_4$ is hydrogen;

$R_3$ is —$C(R_6)(R_7)C_qH_{2q}$—$CH_3$ wherein each of $R_6$ and $r_7$ is hydrogen and q is 3; or Z is —$CO_2R_8$ wherein $R_8$ is hydrogen or methyl.

Another preferred group of compounds of the invention are the compounds of Formula II wherein:

X is $CH_2$—$CH_2$ or —$(CH_2)_4$;

Y is —$CH_2$—$CH_2$ or $CH_2CF_2$;

Z is $CO_2R_8$ wherein $R_8$ is hydrogen or salt thereof, a pharmacologically acceptable metal cation, or methyl;

$R_1$ is hydrogen, alkyl of one to four carbon atoms, inclusive, cyclohexyl or phenyl;

A is —CH=CH— (trans), —C≡C, —$CH_2$—$CH_2$—;

$R_2$ is α—$R_4$,β—$OR_5$; α—$OR_5$, β—$R_4$; =O; or H,H wherein $R_4$ is hydrogen or methyl; and $R_5$ is hydroxy;

$R_3$ is (a) —$C(R_6)(R_7)C_qH_{2q}$—$CH_3$ wherein $R_6$ and $R_7$ are the same and are fluoro or methyl;

(b) —$C(R_6)(R_7)$—B—E wherein $R_6$ and $R_7$ are the same or different and are hydrogen or methyl, and E is

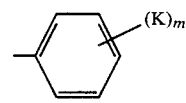

wherein K is fluoro, chloro, trifluoromethyl, or methoxy or ethoxy and m is zero to 2; or (c) cis-2-pentenyl.

The administration of the pharmaceutically useful compounds of the present invention, i.e., compounds of Formulas I and II wherein $R_5$ is other than the hydroxy protecting groups tetrahydropyranyl, trimethylsilyl or tert-butyldimethylsilyl, to humans and animals, particularly mammals, provides a method for the prophylactic or therapeutic treatment of allergy of a reagin or non-reagin mediated nature. These compounds are particularly useful in treating asthma, but any allergy wherein slow reacting substance of anaphylaxis (SRSA) is thought to be involved as a pharmacological mediator of anaphylaxis can be treated. For example, the compounds can be used for treatment of such conditions as allergic rhinitis, food allergy and urticaria as well as asthma.

An effective but essentially non-toxic quantity of these pharmaceutically useful compounds are employed in treatment. The dosage of the compound used in treatment depends on the route of administration, the potency of the particular compound, and the patient, i.e., human or animal, being treated. A dosage schedule for humans of from about 0.1 to about 20 mg of compound in a single dose, administered parenterally or by inhalation in the compositions of this invention are effective for preventing or diminishing the severity of allergy attacks. More specifically, the single dose is from about 0.5 to about 10 mg of compound. The oral dose is from about 2 to about 200 mg in a single dose. More specifically, the single dose is from about 5 to about 100 mg of compound. The dosage is repeated up to four times daily. When administering these pharmaceutically useful compounds to animals the dosage may be adjusted accordingly depending on the weight of the animal being treated.

The pharmaceutically useful compounds are formulated into compositions for administration. The compositions of the present invention are presented for administration to humans and animals in unit dosage forms, such as tablets, capsules, pills, powders, granules, sterile parenteral solutions or suspensions, eye drops, oral solutions or suspensions, and oil in water and water in oil emulsions containing suitable quantities of the compound.

For oral administration, either solid or fluid unit dosage forms can be prepared. For preparing solid compositions such as tablets, the compound of Formula I or II wherein $R_5$ is other than the aforementioned hydroxy protecting groups is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The pharmaceutically useful compound described herein, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. These compounds can be sterilized by exposure to ethylene oxide or an equivalent gas before suspending in the sterile vehicle. Advantageously, a surfactant or wetting agent is included in the composition to facilitate uniform distribution of the compound.

Compositions for inhalation useful in practicing the present invention are of three basic types: (1) a powder mixture preferably micropulverized with particle size, preferably from about 2 to 5 microns; (2) an aqueous solution to be sprayed with a nebulizer; (3) an aerosol with volatile propellant in a pressurized container.

The powders are quite simply prepared by mixing a suitable pharmaceutically useful compound of Formula I or II with a solid base which is compatible with lung tissue, preferably lactose. The powders are packaged in a device adapted to emit a measured amount of powder when inhaled through the mouth.

Aqueous solutions are prepared by dissolving the appropriate compound of the Formula I or II in water and adding salt to provide an isotonic solution and buffering to a pH compatible with inhalation. The solutions are dispersed in a spray device or nebulizer and sprayed into the mouth while inhaling.

Aerosols are prepared by dissolving an appropriate pharmaceutically useful compound of Formula I or II in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to 5 carbon atoms, such as butane and pentane, or a lower alkyl chloride, such as methyl, ethyl or propyl chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoro methane ("Freon 13").

The term "unit dosage form," as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being featurs of the present invention. Examples of suitable unit dosage forms in coated tablets, powder packets, wafers, granulates, cachets, teaspoonfuls, tablespoonfuls, dropperfuls, ampoules, vials, aerosols with metered discharges, segregated multiples of any of the foregoing, and other forms as herein described.

The compounds of Formulas I and II noted hereinabove as being inhibitors of 5-lipoxygenase are administered for use in treating or preventing inflammatory conditions in substantially the same manner and dosage quantities and forms as described above for the treatment of allergy. Oral and parenteral routes of administration to the particular warm blooded animal being treated are preferred. The following compounds are particularly useful in treating inflammation: 6,9-deepoxy-6,9-[[4-(dimethylamino)phenyl]imino]-$\Delta^{6,8}$-prostaglandin $I_1$, methyl ester; 6,9-deepoxy-6,9-[[m-(methylthio)phenyl]imino]-$\Delta^{6,8}$-prostaglandin $I_1$, methyl ester; 6,9-deepoxy-6,9-[[m-(amino)-p-(methyl)-phenyl]amino]-$\Delta^{6,8}$-prostaglandin $I_1$, methyl ester; 6,9-deepoxy-6,9-[[m-(methylthio)phenyl]imino]-$\Delta^{6,8}$-prostaglandin $I_1$, sodium salt; 6,9-deepoxy-6,9-[[m-(methylthio)phenyl]imino]-$\Delta^{6,8}$-prostaglandin $I_1$, diethylamide; 6,9-deepoxy-6,9-[[3-methylthio)phenyl]imino]-$\Delta^{6,8}$-prostaglandin $I_1$, amide; 6,9-deepoxy-6,9-[[3-(methylthio)phenyl]imino]-$\Delta^{6,8}$-prostaglandin $I_1$, methylamide; 6,9-deepoxy-2-hydroxymethyl-1-decarboxy-6,9-[[3-(methylthio)phenyl]imino]-$\Delta^{6,8}$-prostaglandin $I_1$. The compounds of this invention are prepared by procedures generally known in the art. Attention is directed to Chart I wherein the synthetic pathway from known compounds or readily prepared compounds to give compounds of Formula I wherein Z is —COOH is illustrated. The initial starting materials in the synthetic pathway are well known prostacyclin analogs or 6-keto prostacyclin analogs. The process steps from Formulas III through VIII are known from various prior art references, including Belgium Pat. No. 862,547. The various hydroxy groups in the molecule, for example, the 11-position and the 15-position of the molecule, or as occur in substituent group $R_3$ should be protected at various steps of the synthesis by a group resistant to the synthetic conditions, for example, tetrahydropyranyl or a silyl containing ether. The conversion of the 6-keto PGE compound of Formula VIII to the pyrrole of Formula IX is carried out by reacting a Formula VIII compound with an appropriate $R_1NH_2$ amine wherein $R_1$ has the meaning defined in Formulas I and II. As free hydroxyl groups are present in $R_1$ or the substituent groups P, $R_2$ or $R_3$ such function is protected with a group resistant to the reactant conditions, where necessary, with, for example, ether forming groups as described above. It is preferable to maintain the hydroxyl groups of P, $R_1$, $R_2$ and $R_3$ as the free hydroxyl or as the protected hydroxyl from Formula III to VIII and then at VIII converting said group to whatever is desired. Alternatively the conversion can occur at IX.

The conversion of the 6-keto PGE compound of Formula VIII to the pyrrole is carried out in a suitable solvent such as a lower alcohol, ether or amide. Examples of lower alcohols include methanol, ethanol, propanol or isopropanol. Examples of ether include diethyl ether, dioxane and tetrahydrofuran. Examples of amides are dimethylformamide and diethylformamide. The temperature at which the reaction takes place is not unduly significant. Temperature of from about 0° C. to about 50° C. can be employed depending upon the reaction velocity desired. Catalytic quantities of an acid such as a mineral acid, for example, hydrochloric or sulfuric acid, an amine hydrochloride for example or an organic sulfonic acid, for example, para toluene sulfonic acid are generally employed.

The hydroxy protective groups can be removed at this stage or prior to the conversion of the 6-keto compound of Formula VIII to the pyrrole of this invention, i.e., Formula IX wherein $Z_1$ is —COOH, by the standard methods for example acidic hydrolysis for removal of tetrahydropyranyl and contact with an anionic fluoride containing compound for removal of the silyl ether.

By substituting an appropriate 2-decarboxy-2-hydroxymethyl-6-keto-PGE compound of Formula X or a 2-decarboxy-2-(1H-tetrazolyl-5-yl)-6-keto-PGE compound of Formula XI for the 6-keto PGE compound of Formula VIII in the reaction sequence depicted in Chart I, there is obtained respectively pyrroles of this invention as illustrated by Formula IX wherein $Z_1$ is —CH$_2$OH or

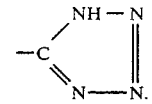

The Formula XI compounds are prepared from either the correspondingly substituted PGF$_{2\alpha}$ derivatives or cyclopentane lactone as described in U.S. Pat. No. 4,205,176. The PGF$_{2\alpha}$ starting materials are prepared by procedures described in U.S. Pat. No. 3,636,120. The 2-decarboxy-2-(1H-tetrazol-5-yl)-6-keto-PGE compounds of Formula XI are prepared as described in U.S. Pat. No. 4,205,178. The starting materials for the Formula XI compounds are obtained conveniently as described in U.S. Pat. No. 3,932,389. In the preparation of the compounds of Formulas X or XI or in the conversion of said compounds to pyrrole products of this invention the various hydroxy groups occurring therein are protected, where necessary, as described hereinabove, i.e., with such groups as trimethylsilyl, tetrahydropyranyl or tert-butyldimethylsilyl. Selective protection of the hydroxy groups may be appropriate, as for example in preparing compounds from Formula X wherein free hydroxy groups are present in any of the substituent groups $R_1$, P, $R_2$ or $R_3$ and the 2-hydroxymethyl moiety is derivatized to provide compounds of Formulas I or II wherein $R_5$ is other than hydrogen. Generally known reaction methods are described hereinabove for the selective removal of hydroxy protecting groups. The compounds of Formula IX wherein $Z_1$ is —CH$_2$OH or —COOH can be converted to compounds of Formulas I and II wherein $R_5$ or $R_8$ or $R_{19}$ is other than hydrogen by general procedures well known in the art. The compounds of Formula IX wherein $Z_1$ is —COOH can also be converted conveniently to compounds of Formula I wherein Z is —CONR$_{13}$R$_{14}$ or if desired compounds wherein Z is —CH$_2$OR$_5$.

The pyrrole products of the invention are isolated, for example, by aqueous dilution of the reaction mixture, extraction of the products into ethyl acetate or etherial solvents with subsequent evaporation of the solvent to provide the crude product. Purification of the product is achieved by crystallization or chromatography on, for example, silica gel using ethyl acetate-hexane mixtures as the solvent.

During the conversion of compounds of Formulas VIII, X or XI wherein P is hydroxy to the corresponding pyrrole the correspondingly substituted compounds of Formula I wherein P is hydroxy are obtained as well as the correspondingly substituted compounds of Formula II. The Formula II compounds thus produced are isolated chromatographically, e.g., by using silica gel and an ethyl acetate-cyclohexane solvent system.

The compounds of Formula II are useful as intermediates in the preparation of compounds of Formula I wherein P is hydrogen. The appropriate Formula II compound is reduced to the Formula I compound using platinum oxide or palladium on carbon catalysis in an alcoholic or ester solvent at atmosphereic pressure and low temperatures ranging from about $-70°$ C. to $-20°$ C. Sodium nitrite (0.1% alcoholic solution) is conveniently employed to avoid hydrogenolysis of allylic substituents. This method is especially applicable to the synthesis of the compounds of Formula I containing substituent groups not susceptible to reduction, e.g. $-C\equiv C-$ or $NO_2$ groups. Concomitant reduction of these groups and the cyclopentene ring may be in certain instances desirable.

The following are illustrative examples of compounds of the invention. An appropriate amine of the formula $R_1NH_2$ wherein $R_1$ has the meaning defined in Formulas I and II is reacted with a compound of Formula VIII, X or XI having the following structural features:

15-methyl;
16-methyl;
16,16-dimethyl-;
16-fluoro-;
16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-phenoxy-18,19,20-trinor-;
16-methyl-16-phenoxy-18,19,20-trinor-;
16-methyl-13,14-didehydro-;
16,16-dimethyl-13,14-didehydro-;
16-fluoro-13,14-didehydro-;
17-phenyl-18,19,20-trinor-13,14-didehydro-;
17-(m-trifluoromethylphenyl)-18,19,20-trinor-13,14-didehydro:;
17-(m-chlorophenyl)-18,19,20-trinor-13,14-didehydro-;
17-(p-fluorophenyl)-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-phenoxy-18,19,20-trinor-13,14-didehydro-;
16-methyl-16-phenoxy-18,19,20-trinor-13,14-didehydro-;
13,14-dihydro-;
16-methyl-13,14-dihydro-;
16,16-dimethyl-13,14-dihydro-;
16-fluoro-13,14-dihydro-;
16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
16-methyl-16-phenoxy-18,19,20-trinor-13,14-dihydro-;
2,2-difluoro-;
2,2-difluoro-16-methyl-;
2,2-difluoro-16,16-dimethyl-;
2,2-difluoro-16-fluoro-;
2,2-difluoro-16,16-difluoro-;
2,2-difluoro-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor-;
2,2-difluoro-16-methyl-17-phenyl-18,19,20-trinor-;
2,2-difluoro-16,16-dimethyl-17-phenyl-18,19,20-trinor-;
2,2-difluoro-16-fluoro-17-phenyl-18,19,20-trinor-;
2,2-difluoro-16,16-difluoro-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2-difluoro-16-fluoro-13,14-didehydro-;
2,2-difluoro-16,16-difluoro-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;

2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-16-methyl-13,14-dihydro-;
2,2-difluoro-16,16-dimethyl-13,14-dihydro-;
2,2,16-trifluoro-13,14-dihydro-;
2,2,16,16-tetrafluoro-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2-trifluoro-17-phenyl-18,19,20-trinor-13,14-dihydro-;
2,2,16,16-tetrafluoro-17-phenyl-18,19,20-trinor-13,14-dihydro-;
2,2-difluoro--16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy)-17,18,19,20-tetranor-13,14-dihydro-;
2,2-difluoro-16-phenoxy-18,19,20-trinor-13,14-dihydro;
2,2-difluoro-16-phenoxy-18,19,20-trinor-13,14-dihydro-;
16-methyl-cis-13-;
16,16-dimethyl-trans-13-;
16-fluoro-cis-13-;
16,16-difluoro-trans-13-;
17-phenyl-18,19,20-trinor-cis-13-;
17-(m-trifluoromethylphenyl)-18,19,20-trinor-trans-13-;
17-(m-chlorophenyl)-18,19,20-trinor-cis-13-;
17-(p-fluorophenyl)-18,19,20-trinor-trans-13-;
16-methyl-17-phenyl-18,19,20-trinor-cis-13-;
16,16-dimethyl-17-phenyl-18,19,20-trinor-trans-13-;
16-fluoro-17-phenyl-18,19,20trinor-cis-13-;
16,16-difluoro-17-phenyl-18,19,20-trinor-trans-13-;
16-phenoxy-17,18,19,20-tetranor-cis-13-;
16(m-trifluoromethylphenoxy)-17,18,19,20-tetranor-trans-13-;
16-(m-chlorophenoxy)-17,18,19,20-tetranor-cis-13-;
16-(p-fluorophenoxy)-17,18,19,20-tetranor-trans-13-;
16-phenoxy-18,19,20-trinor-cis-13-;
16-methyl-16-phenoxy-18,19,20-trinor-trans-13-;
2,2-difluoro-cis-13-;
2,2-difluoro-16-methyl-trans-13-;
2,2-difluoro-16,16-dimethyl-cis-13-;
2,2-difluoro-16-fluoro-trans-13-;
2,2-difluoro-16,16-difluoro-cis-13-;
2,2-difluoro-17-phenyl-18,19,20-trinor-trans-13-;
2,2-difluoro-17-(m-trifluoromethylphenyl)-18,19,20-trinor-cis-13-;
2,2-difluoro-17-(m-chlorophenyl)-18,19,20-trinor-trans-13-;
2,2-difluoro-17-(p-fluorophenyl)-18,19,20-trinor-cis-13-;
2,2-difluoro16-methyl-17-phenyl-18,19,20-trinor-trans-13-;
2,2-difluoro-16,16-dimethyl-17-phenyl-18,19,20-trinor-cis-13-;
2,2-difluoro-16-fluoro-17-phenyl-18,19,20-trinor-trans-13-;
2,2-difluoro-16,16-difluoro-17-phenyl-18,19,20-trinor-cis-13-;
2,2-difluoro-16-fluoro-17-phenyl-18,19,20-trinor-trans-13-;
2,2-difluoro-16,16-difluoro-17-phenyl-18,19,20-trinor-cis-13-;
2,2-difluoro-16-fluoro-18-phenyl-19,20-dinor-trans-13-;
2,2-difluoro-16,16-difluoro-18-phenyl-19,20-dinor-cis-13-;
2,2-difluoro-16-phenoxy-17,18,19,20-tetranor-trans-13-;
2,2-difluoro-16-(m-trifluoromethylphenoxy)-17,18,19,20-tetranor-cis13-;
2,2-difluoro-16-(m-chlorophenoxy)-17,18,19,20-tetranor-trans-13-;
2,2-difluoro-16-(p-fluorophenoxy)-17,18,19,20-tetranor-cis-13-;
2,2-difluoro-16-phenoxy-18,19,20-trinor-trans-13-;
2,2-difluoro-16-methyl-16-phenoxy-18,19,20-trinor-cis-13-;
2,3-didehydro-;
trans-2,3-dehydro-;
15-keto-2,2-difluoro-;
15-dihydro-;
15-methoxy-;
15-methoxy-13,14-dihydro-;
15-acetyl-;
15-methoxy-;
15-acetyl-17-phenoxy-18,19,20-trinor-;
15-acetyl-13trans-;
20 methyl-;
20nor-;
19,20-dinor-;
15-ethyl-18,19,20-trinor-;
15-methyl-18,19,20-trinor-;
13,14-didehydro;
2-trans-20-nor-;
15-ethyl-15-methoxy-18,19,20-trinor-;
16-difluoro-ethylene-19-phenyl-20-nor-;
18-p-chlorophenyl-20-nor-;
cis-17,18-dehydro-;
2,2-difluoro-cis-17,18-dehydro-;
13,14-dihydro-cis-17,18-dehydro-;
trans-2-cis-17,18-dehydro-;
1a, 1b-dihomo-cis-17,18-dehydro-;
trans-2-3a,3b-dihomo-trans-13,14-dehydro-16-phenoxy-18,19,20-trinor.

CHART I

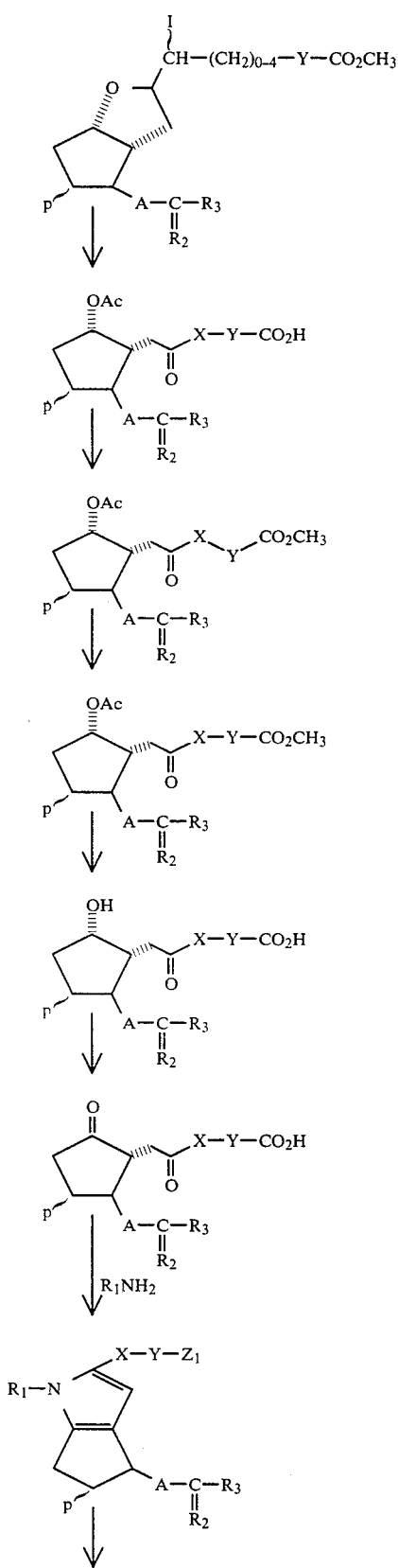

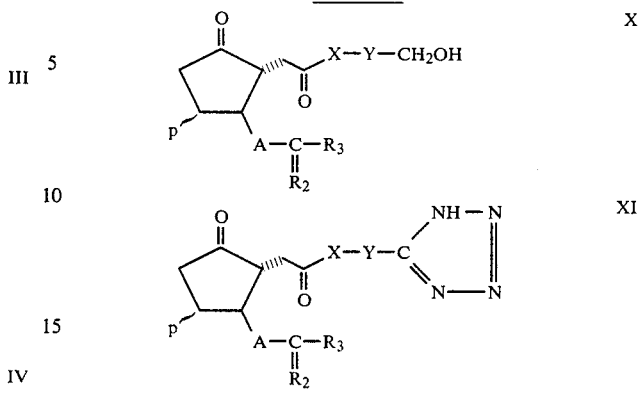

The following specific examples illustrate the preparation of compounds of the invention.

EXAMPLE 1

9-Deoxy-6,9-N-phenylimino-$\Delta^{6,8}$-PGI-hd 1 methyl ester, 11,15-diacetate (a) 5ξ-Iodo-9-deoxy-6ξ,9α-epoxy-11,15-bis-dimethyl-t-butylsilyl ether A solution of 5ξ-iodo-9-deoxy-6ξ,9α-epoxy PGF$_1$α methyl ester (11.0 g) in DMF (50 ml) is treated with imidazole (8.86 g) and t-butyldimethylchlorosilane (7.85 g) and reacted for two hours. The suspension is diluted with H$_2$O and extracted with ethyl acetate. Drying and evaporation of the extract gave 15 g of a pale yellow oil. Purification on silica gel (360 g) with 97% hexane—3% ethyl acetate (260 ml fractions) gives 10.9 g of 1a.

(b) 6-Keto-PGF$_1$αbis-dimethyl-t-butylsilyl ether methyl ester

A solution of 1a (10.9 g) in toluene (50 ml) is treated with diazabicyclononene (12.5 ml) and reacted for 19 hours. Additional reagent (8.2 ml) is added and the suspension reacted for six hours. The reaction is diluted with ethyl acetate, partitioned with H$_2$O, dried and evaporated to a green oil.

The crude oil is hydrolyzed in acetonitrile (5 ml) with 4% acetic acid in 90% aqueous acetonitrile for 45 minutes, diluted with 0.2 M KHSO$_4$, extracted with ether, and the combined extracts washed with H$_2$O. Drying and evaporation of solvent give a two-product mixture (8.96 g).

Purification on silica gel (440 g) with 85% hexane—15% ethyl acetate (40 ml fractions) gives 1.65 g of impure hemi-acetal; 7:3 hexane:ethyl acetate elution (fractions 10–43) gives 7.1 g of (b) above containing 25–30% of the hemiacetal, R$_f$0.40 and 0.77, respectively in 3:1 cyclohexane; ethyl acetate; R$_f$0.08 and 0.31, respectively in 9:1 cyclohexane:ethyl acetate.

(c) 6-Keto-PGF$_1$α9-acetate-11,15-bis-t-butyldimethylsilyl ether methyl ester

A solution of crude 1b (5.1 g) in pyridine (20 ml) is treated with acetic anhydride and reacted for 65 hours. The solution is cooled, diluted with 5% NaCl and extracted with ether. The extract is washed, dried and evaporated to yield crude (c) as a pale yellow oil (5.78 g).

Fractionation on silica gel (425 g) with 9:1 hexane:ethyl acetate (fractions 1–19) and 8.5:1.5 hexane:ethyl acetate (fractions 20–46) gives (c) (3.83 ) in fractions 21–29.

(d) 6-Keto-PGF$_1\alpha$11,15-bis-t-5-butyldimethylsilyl ether

A solution of 1c (1.43 g) in dimethylformamide (90 ml) is treated with 2.2N NaOH (10 ml) and the turbid mixture with H$_2$O (12 ml). The solution is heated at 80°–87° C. for 1.5 hours, cooled, acidified with 0.2 M KHSO$_4$ and extracted with ethyl acetate. The extract is washed, dried and evaporated to yield (d) above (1.01 g) as a pale yellow oil, R$_f$0.27 in solvent 2:1 cyclohexane; organic layer from 9:2:5:10 ethyl acetate:acetic acid:cyclohexane:water. Neat storage at 4° C. produces an impurity (ca. 20%) at R$_f$0.34.

The sample is combined with product (2.8 g) from duplicate hydrolysis and purified on CC-4 silica gel (430 g) with 9:1 hexane: ethyl acetate collecting 48 ml fractions for fractions 1–84 and 8.5:1.5 for fractions 85–168 (55 ml fractions). Fractions 130–168 provide 2.58 g (61%) of (d).

(e) 6-Keto-PGE$_1$, 11,15-bis-t-butyldimethyl silyl ether

A solution of (d) above (2.5 g) in acetone (45 ml) at −40° C. was treated with 2.67 M Jones reagent (3.25 ml), brought to −20° C. during eight minutes and reacted and reacted at −20° C. for 75 minutes. The suspension is diluted with cold 5% NaCl, extracted with ether and the combined extracts are washed with 5% NaCl. Drying and evaporation of solvent gave 2.0 g of yellow oil. Fractionation on CC-4 silica gel (210 g) with 8.5:1.5 (50 ml fractions) removes polar impurities. Fractions 23–50 give pure (e) (0.85 g), R$_f$ 0.25 in 2:1 cyclohexane:organic layer from 9:2:5:10 ethyl acetate:acetic acid:cyclohexane:water.

(f) 9-Deoxy-6,9-N-phenylimino-$\Delta^{6,8}$-PGI$_2$11,15-bis-t-butyldimethylsilyl ether methyl ester A solution of (e) above (0.85 g) in ethanol (2 ml) is treated with 1 M aniline in ethanol (10 ml) and 0.1 M pyridine hydrochloride in methylene chloride (0.08 ml) and reacted for 26 hours. The solution is diluted with ether, washed with 0.2 M KHSO$_4$ and 5% NaCl solutions, dried and evaporated to yield crude acid. Without purification, the prepared acid is esterified with excess ethereal diazomethane to yield crude (f) (0.90 g).

Fractionation on CC-4 silica gel with 95:5 hexane:ethyl acetate (18 ml fractions) gives pure (f) above (0.52 g), R$_f$0.53, 0.66 in 2:1 cyclohexane:organic layer from 9:2:5:10 ethyl acetate:acetic acid:cyclohexane:water, and 9:1 cyclohexane:ethyl acetate, respectively, in fractions 6–13. Pure acid (0.116 g) is obtained in fractions 29–63 R$_f$ 0.45 in 2:1 cyclohexane:organic layer from 9:2:5:10 ethyl acetate:acetic acid:cyclohexane:water.

(g) 9-Deoxy-6,9-N-phenylimino-$\Delta^{6,8}$PGI$_1$ methyl ester

A solution of 1f (0.51 g) in tetrahydrofuran (THF) is treated with 1.2 M tetrabutylammonium fluoride in THF (5 ml) and reacted for 1.5 hours. The dark solution is diluted with ether, washed with 0.2 M KHSO$_4$ and 5% NaCl solutions, dried and evaporated. The residue (0.42 g) is purified on CC-4 silica gel (60 g), collecting 17 ml fractions. Fractions 95–120 (3:2 hexane:ethyl acetate) provides 78 mg of (g), (product compound), m.p. 95.5° C. after ether-hexane crystallization.

IR (mull) 965, 1060, 1495, 1605, 1745, 2975, 3425 cm$^{-1}$.

Ultraviolet (Ethanol) 233 ($\epsilon$ 11,400) nm.

(h) 9-Deoxy-6,9-N-phenylimino-$\Delta^{6,8}$-PGI$_1$ methyl ester, 11,15-diacetate A solution of 1g (2.15 g, 5.0 mmoles) in 15 ml of pyridine, 5 ml of acetic anhydride and 4-dimethylaminopyridine is reacted at ambient temperature for 2.5 hours after which the solution is diluted to 200 ml with ice water and stirred without precipitation. The oily residue was extracted into ethyl acetate, washed with 5% NaCl, 5% NaHCO$_3$, 0.2% KHSO$_4$ solution and finally with water. Drying and evaporation of the solvent gives (h) (3.35 g) after carbon tetrachloride evaporation. The product is homogenous by thin layer chromatography (3:1 cyclohexane, ethyl acetate).

NMR: (CDCl$_3$)$\delta$0.90 (t,3,CH$_3$), 1.0–1.7 (m,12,CH$_2$,CH), 2.00 (s, CH$_3$CO), 1.8–2.8 (m,12,CH,CH$_2$,COCH$_3$), 2.8–3.3 (m,1,CH), 3.56 (s,3,CO$_2$CH$_3$), 5.0–6.0 (m,3,CH-oAc), CH=CH,pyrrole-H,7.0–7.5 (m,5, ArH).

IR (natural film): 1735 (C=O), 1600, 1500. 1440, 1370, 1240, 1025, and 970 cm$^{-1}$.

EXAMPLE 2

6,9-Deepoxy-10,11-didehydro-11-deoxy-6,9-[(p-nitrophenyl)imino]$\Delta^{6,8}$prostaglandin I$_1$ methyl ester A solution of 115 mg (0.3 mmoles of 6-keto PGE$_1$ methyl ester, 0.5 ml of absolute ethanol, 83 mg (0.6 mmoles) of p-nitroaniline and a small amount of pyridine.HCl is stirred at about 25° C. in the dark and under a nitrogen atmosphere for about 24 hours. The reaction mixture turns dark. The solvent is evaporated and the residue is chromatographed over silica gel (20 g) eluting with 50% ethyl acetate-50% mixed hexanes, collecting 2 ml fractions. Fractions 61–100 were further chromatographed over silica gel (2 g) eluting with 10% acetone - 90% methylene chloride followed by 20% acetone - 80% methylene chloride collecting 1 ml fractions. Fractions 21–60 are combined and evaporated to give the desired product. R$_f$0.55, thin layer on silica gel 60 using 10% acetone-90% methylene chloride.

EXAMPLE 3

6,9-Deepoxy-6,9-[(phenylmethyl)imino]-$\Delta^{6,8}$ prostaglandin I$_1$ methyl ester When in the procedure of Example 2 an appropriate amount of benzylamine is substituted for p-nitroaniline, and the reaction mixture is stirred for 3.5 hours the title product is obtained which is purified by chromatography over silica gel (20 g) eluting with 70% ethyl acetate - 30% mixed hexanes, and collecting fractions 20–40 of 2 ml each. R$_f$0.85, thin layer on silica gel 60 using 70% ethyl acetate - 25% mixed hexanes.

EXAMPLE 4

6,9-[(acetamidophenyl)imino]$\Delta^{6,8}$ prostaglandin I$_1$ methyl ester

When in the procedure of Example 2 an appropriate amount of p-acetamidoaniline is substituted for p-nitroaniline the title product is obtained and is purified by chromatography over silica gel (100 g) eluting with 5% methanol - 95% methylene chloride and 10% methanol - 90% methylene chloride, collecting and evaporating fractions 56–78 of 20 ml each. R$_f$0.30, thin layer on silica gel 60 using 40 acetone - 60% mixed hexanes.

EXAMPLE 5

6,9-Deepoxy-6,9-[(p-ethoxyphenyl)imino]-$\Delta^{6,8}$ prostaglandin $I_1$ methyl ester (a) 6,9-Deepoxy-6,9-[(p-ethoxyphenyl)imino]-$\Delta^{6,8}$ prostaglandin $I_1$ methyl ester, 11,15-di(tert-butyldimethylsilyl) ether A solution 0.72 g (1.18 mmole) of 6-keto $PGE_1$ methyl ester, 11,15-di(tert-butyldimethylsilyl) ether, 1 ml of methanol, a small amount of pyridine.HCl, 250 mg of magnesium sulfate, and 178 mg (1.3 mmole) of p-phenetidine is stirred at about 25° C. in the dark and under a nitrogen atmosphere for about 18 hours. The reaction mixture is filtered, and the filtrate is evaporated leaving a residue which is chromatographed over silica gel (100 g) eluting with 10% ethyl acetate - 90% mixed hexanes. Fractions 21–32 were collected yielding 710 mg of the title product. $R_f$ 0.55, thin layer on silica gel 60 using 10% ethyl acetate - 90% mixed hexanes.

(b) 6,9-Deepoxy-6,9-[(p-ethoxyphenyl)imino]$\Delta^{6,8}$ prostaglandin $I_1$ methyl ester The 710 mg of compound 5a and 1.38 g of tetra-n-butylammonium fluoride is stirred at 0° C. under a nitrogen atmosphere in the dark for 2 hours, then stirring is continued at about 25° C. for about 36 hours. The reaction mixture is partitioned between ethyl acetatebrine. The aqueous layer is collected and extracted with ethyl acetate from which the organic layer is dried over magnesium sulfate, filtered and evaporated. The resulting residue is chromatographed over silica gel (80 g) eluting with 70% ethyl acetate - 30% mixed hexanes. Fractions 19–38 of 20 ml each yield 410 mg of the title product. $R_f$ 0.40, thin layer on silica gel 60 using 60% ethyl acetate - 40% mixed hexanes.

Similarly, when m-phenetidine is used in place of p-phenetidine in Example (5a) and the procedures of (5a) and (5b) followed, the corresponding m-ethoxyphenyl derivative is obtained. $M^+$ (trimethylsilyl derivative): 627.3753, calculated for $C_{35}H_{57}NO_5Si_2$: 627.3775.

EXAMPLE 6

6,9-Deepoxy-6,9-[(3,4-dimethoxyphenyl)imino]$\Delta^{6,8}$ prostaglandin $I_1$ methyl ester When in the procedure of Example 5a an appropriate amount of 2,4-dimethoxyaniline is substituted for p-phenetidine, 6,9-deepoxy-6,9-[(3,4-dimethoxyphenyl)imino]$\Delta^{6,8}$ prostaglandin $I_1$ methyl ester, 11,15-di(tert-butyldimethylsilyl) ether is obtained, and when said ether is substituted in Example (5b) for the product of Example (5a), the title product is obtained. $R_f$ 0.50, thin layer on silica gel 60 using 70% ethyl acetate - 30% mixed hexanes.

EXAMPLE 7

6,9-Deepoxy-6,9-[(3-amino-4-methylphenyl)imino]$\Delta^{6,8}$ prostaglandin $I_1$ methyl ester When in the procedure of Example (5a) an appropriate amount of 2.4-diamenotoluene is substituted for p-phenetidine 6,9-deepoxy-6,9-[(3-amino-4-methylphenyl)imino]$\Delta^{6,8}$ prostaglandin $I_1$ methyl ester, 11,15-di(tert-butyldimethylsilyl) ether is obtained, and when said ether is substituted in Example (5b) for the product of Example (5a), the title product is obtained. $R_f$ 0.25, thin layer on silica gel 60 using 70% ethyl acetate - 30% mixed hexanes.

EXAMPLE 8

6,9-Deepoxy-6,9-[(4-acetylphenyl)imino]$\Delta^{6,8}$ prostaglandin $I_1$ methyl ester When in the procedure of Example (5a) an appropriate amount of p-aminoacetophenone is substituted for p-phenetidine, 6,9-deepoxy-6,9-[(4-acetylphenyl)imino]-$\Delta^{6,8}$ prostaglandin $I_1$ methyl ester, 11,15-di(tert-butyldimethylsilyl) ether is obtained, and when said ether is substituted in Example (5b) for the product of Example (5a), the title product is obtained. $R_f$ 0.15, thin layer on silica gel 60 using 50-ethyl acetate - 50% mixed hexanes.

EXAMPLE 9

6,9-Deepoxy-6,9-[(p-hydroxyphenyl)imino]$\Delta^{6,8}$ prostaglandin $I_1$ methyl ester (a) 6,9-deepoxy-6,9-[(p-hydroxyphenyl)imino]$\Delta^{6,8}$ prostaglandin $I_1$ methyl ester, 11,15-di-(tetrahydropyranyl) ether A mixture of 550 mg (1 mmole) of the 11,15-di-(tetrahydropyranyl) ether of 6-keto $PGE_1$, 3ml of absolute ethanol, 14 mg of pyridine.HCl, and 1.09 g of p-aminophenol is stirred at about 25° C. under a nitrogen atmosphere in the dark for about 24 hours. The reaction mixture is evaporated, and the residue chromatographed over silica gel (150 g) eluting with 30% ethyl acetate - 70% mixed hexanes and 40% ethyl acetate - 60% mixed hexanes. Fractions 49–72 of 20 ml each give 620 mg of the title product (9a). The 620 mg of product from (9a) is heated to 40° C. for 2.5 hours in a solution of 4 ml of acetic acid and 2 ml of water. The reaction mixture is diluted with toluene, and the solvent evaporated leaving a dark residue which is dissolved in ethyl acetate. The organic solution is washed with brine containing sodium bicarbonate and the layers are separated. The ethyl acetate layer is dried over sodium sulfate and evaporated to give the product which is purified by chromatography over silica gel (70 g) eluting with 70% ethyl acetate - 30% mixed hexanes. Fractions 35–60 of 10 ml each yield 139 mg of 6,9-deepoxy-6,9-[(p-hydroxyphenyl)imino]-$\Delta^{6,8}$ prostaglandin $I_1$ methyl ester. $R_f$ 0.30, thin layer on silica gel 60 using 70% ethyl acetate - 30% mixed hexanes.

EXAMPLE 10

6,9-Deepoxy-10,11-didehydro-11-deoxy-6,9-N-phenylimino-$\Delta^{6,8}$-$PGI_2$-15-t-butyldimethylsilyl ether methyl ester A solution of 6-keto-$PGE_1$, 11,15-bis-t-butyldimethylsilyl ether methyl ester (1.0 g) in anhydrous methanol (1.0 ml), aniline (0.15 ml) and pyridine hydrochloride (21 mg) is cooled to 0° C. to 5° C. and reacted for 16 hours. The solution is diluted with ethyl acetate and washed with 1% sodium bisulfate, 5% sodium bicarbonate solution, dried and evaporated. The residue (1.47 g) is purified on silica gel (30 g) with 9:1 heptane:ethyl acetate collecting 20 ml fractions to give the title product.

EXAMPLE 11

6,9-Deepoxy-11-deoxy-6,9-N-(4-aminophenyl)-immuno-13,14-dihydro-$\Delta^{6,8}$-$PGI_1$ methyl ester A solution of 6,9-deepoxy-10,11-didehydro-11-deoxy-6,9-[(p-nitrophenyl)imino]-$\Delta^{6,8}$-$PGI_1$ methyl ester (30 mg) in 95% ethanol (10 ml) is treated with 10% palladium on carbon (30 mg) and hydrogenated at atmospheric pressure. When hydrogen uptake ceases, catalyst is filtered and the solution evaporated to yield the title compound.

EXAMPLE 12

6,9-Deepoxy-6,9-[(phenylmethyl)imino]-$\Delta^{6,8}$-prostaglandin $I_1$

A solution of 6,9-deepoxy-6,9-[(phenylmethyl)imino]-$\Delta^{6,8}$-prostaglandin $I_1$ methyl ester (0.320 g) in 20 ml of methanol and 4 ml of 1N sodium hydroxide is reacted at 25° C. for 18 hours. The solution is acidified with 1M citric acid and the precipitate collected and subsequently recrystallized from methylene chloride-hexane to give the title compound.

EXAMPLE 13

(a) $\Delta^{6,8}$-Prostaglandin $I_1$, 6,9-deepoxy-6,9-[[m-(methylthio)phenyl]imino]-, methyl ester, 11,15-dimethyl-t-butylsilyl ether A 2.0 g (3.28 mM) quantity of 6-keto-PGF$_{1\alpha}$-11,15-bis-dimethyl-t-butylsilyl ether methyl ester, 460 mg (3.31 mM) of 3-methyl-mercaptoaniline, a crystal of pyridine hydrochloride, 500 mg MgSO$_4$ and 2 ml MeOH was stirred at room temperature under nitrogen in the dark for 29 hours. The reaction mixture was filtered, washing the solid with EtOAc. The filtrate was then evaporated under vacuum. The crude product was chromatographed over 150 g silica gel, eluting with 10% EtOAc - 90% SSB. Fractions of 20 ml were collected, analyzing them by TLC. Fractions 19-30 contained the title product (a).

TLC: 10% EtOAc - 90% SSB; silica gel. R$_f$, 0.73.

NMR: (CCl$_4$, δ) 0.1 (2s, 12H); 0.5-1.1 ((s+m, 20H); 1.1-1.8 (m, 13H); 1.9-3.1 (s+m, 9H); 3.3-3.7 (s+m, 4H); 3.9-4.2 (m, 1H); 4.2-4.7 (m, 1H); 5.5-5.9 (s+m, 3H); 6.8-7.5 (m, 4H).

Fractions 35-44 yielded $\Delta^{6,8}$-prostaglandin $I_1$, 6,9-deepoxy-11-O-methyl-[[m-(methylthio)phenyl]imino]-, methyl ester, 15-dimethyl-t-butylsilyl ether. R$_f$: 0.61.

NMR: (CCl$_4$, δ) 0.05 (s, 6H); 0.9 (s, 12H); 2.5 (s,3H); 3.3 (s, 3H); 3.55 (s, 3H); 3.7-4.2 (broad, 2H); 5.4-5.75 (m, 3H); 6.8-7.4 (m, 4H); 1.1-3.7 (m, 19H).

(b) $\Delta^{6,8}$-Prostaglandin $I_1$, 6,9-deepoxy-6,9-[[m-(methylthio)phenyl]imino]-, methyl ester A 600 mg (0.84 mM) quantity of the silyl ether from (a) above, 36 ml isopropanol, 4.5 ml H$_2$O and 4.5 ml 1N HCl was stirred at room temperature under N$_2$ in the dark for 1.5 hours. TLC indicated that the hydrolysis was progressing cleanly and therefore another 610 mg (0.86 mM) silyl ether was added as well as 36 ml isopropanol, 4.5 ml H$_2$O and 4.5 ml 1N HCl. The reaction was continued for 5 hours.

The reaction mixture was partitioned between EtOAc - 5% NaHCO$_3$-brine. The layers were separated and the organic layer washed with brine, dried over MgSO$_4$ and evaporated under vacuum.

The crude product was chromatographed over 120 g silica gel, eluting with 500 ml 60% EtOAc - 40% SSB and 500 ml of 70% EtOAc - 30% SSB. Fractions of 20 ml were collected, analyzing them by TLC. The product was found in fractions 29-46, which upon combining and evaporating under vacuum left 0.57 g solid, 69% yield.

TLC: 60% EtOAc—40% SSB; silica gel. R$_f$, 0.33.

IR: C=O1735; OH—3300,3375.

NMR: (CDCl$_3$, δ) 0.7-1.0 (t, 3H); 1.1-3.2 (m, 18H); 2.4 (s, 3H); 3.3-3.5 (broad, 1H); 3.6 (s, 3H); 3.6-3.9 (broad, 2H); 3.9-4.2 (broad, 1H); 4.2-4.6 (q, 1H); 5.6-5.7 (m, 2H); 5.75 (s, 1H); 6.85-7.45 (m, 4H). cl EXAMPLE 14

$\Delta^{6,8}$-Prostaglandin $I_1$, 6,9-deepoxy-11-O-6,9-[[m-(methylthio)phenyl]imino]-, methyl ester A 250 mg (0.408 mM) quantity of $\Delta^{6,8}$-prostaglandin $I_1$, 6,9-deepoxy-11-O-methyl-[[m-(methylthio)phenyl]imino]-, methyl ester, 15-dimethyl-t-butyl silyl ether, 12 ml isopropanol, 1.5 ml H$_2$O and 1.5 ml 1N HCl was stirred at room temperature under nitrogen in the dark for 6.5 hours. The reaction mixture was partitioned between EtOAc - 15 ml 5% NaHCO$_3$ - brine. The layers were separated and the EtOAc layer washed with brine, dried over MgSO$_4$ and evaporated under vacuum.

The crude product was chromatographed over 50 g silica gel, eluting with 40% EtOAc - 60% SSB. Fractions of 20 ml were collected, analyzing them by TLC. The product was found in fractions 12-16, which upon combining and evaporation under vacuum left 60 mg, 29% yield.

TLC: 10% EtOAc - 90% SSB; silica gel. R$_f$ of starting material: 0.65. R$_f$ of product: 0.20.

IR: OH - 3400 broad; C=O - 1735.

NMR: (CDCl$_3$, δ) 0.9 (t, 3H); 2.5 (s, 3H); 3.4 (s, 3H); 3.65 (s, 3H); 4.0-4.3 (m, 2H); 5.7-5.8 (m, 2H); 5.85 (s, 1H); 6.95-7.5 (m, 4H); 1.1-3.3 (m, 20H).

EXAMPLE 15

$\Delta^{6,8}$-Prostaglandin $I_1$, 6,9-deepoxy-6,9-[[m-(methylthio)phenyl]imino]-, sodium salt A 10 mg (0.021 mM) quantity methyl ester of Example 13(b) was reacted at room temperature in the dark 500 μl MeOH and 35 μl 1N NaOH for 4 days. The solvent was evaporated under a stream of nitrogen to give the title compound.

TLC: Acid dipped plate; 60% EtOAc - 40% SSB; silica gel; R$_f$ of product 0.38.

EXAMPLE 16

$\Delta^{6,8}$-Prostaglandin $I_1$, 6,9-deepoxy-6,9-[[p-(acetylthio)phenyl]imino]-, methyl ester A 2.0 g (3.28 mM) quantity of 6-keto-PGF$_{1\alpha}$-11,15bis-dimethyl-t-butylsilyl ether methyl ester, 820 mg (6.56 mM) 4-aminothiophenol, a small crystal of pyridine hydrochloride, 2ml MeOH and 500 mg MgSO$_4$ was stirred at room temperature under N$_2$ in the dark for 22 hours. The reaction mixture was filtered, washing the solid with EtOAc. The filtrate was evaporated under vacuum and the residue chromatographed over 150 g silica gel, eluting with 10% EtOAc - 90% SSB. Fractions of 20 ml were collected, analyzing them by TLC. Fractions 21-35 gave $\Delta^{6,8}$-prostaglandin $I_1$, 6,9-deepoxy-6,9-[[p-(mercapto)phenyl]imino-, methyl ester which combining and evaporating left 1.87 g oil, 82% yield.

TLC: 10% EtOAc - 90% SSB; silica gel. R$_f$, 0.75.

NMR: (CCl$_4$, δ) 0.1 (2s, 12H); 0.6-1.1 (m+s, 20H); 1.1-1.8 (m, 13H); 1.9-3.1 (m, 6H); 3.2-3.7 (s+m, 5H);

3.9–4.25 (m, 1H); 4.25–4.6 (m, 1H); 5.4–5.9 (s+m, 3H); 6.9–7.7 (m, 4H).

(b) A 1.87 g (2.68 mM) quantity of the thiol from (a) above, 4 ml pyridine and 0.8 ml acetic anhydride was stirred at room temperature under $N_2$ in the dark for 1 hour. A few drops of water were added and the reaction mixture was stirred for 15 minutes. It was then diluted with EtOAc and washed with 1N HCl, 5% $NaHCO_3$ and brine and dried over $Na_2SO_4$ and evaporated under vacuum.

The crude product was chromatographed over 150 g silica gel, eluting with 10% EtOAc - 90% SSB. Fractions of 20 ml were collected, analyzing them by TLC. Fractions 25–50 contained $\Delta^{6,8}$-prostaglandin $I_1$, 6,9-deepoxy-6,9-[[p-(acetylthio)phenyl]imino]-, methyl ester, 11,15-bis-dimethyl-t-butylsilyl ether. Fractions 25–50 were combined and evaporated under vacuum, leaving 1.51 g yellow oil, 76% yield.

TLC: 10% EtOAc - 90% SSB; silica gel. $R_f$, 0.47.

NMR: ($CCl_4$, δ) 0.1 (2s, 12H); 0.6–1.2 (s+m, 21H); 1.2–2.0 (m, 12H); 2.0–3.2 (s+m, 9H), 3.3–3.9 (s+m, 4H); 3.9–4.3 (m, 1H); 4.3–4.7 (m, 1H); 5.6–6.1 (s+m, 3H); 7.1–7.9 (m, 4H).

(c) A 1.51 g (2.04 mM) quantity of the silyl ether from (b) above, 72 ml isopropanol, 9 ml $H_2O$ and 9 ml 1N HCl was stirred at room temperature under $N_2$ in the dark for 5 hours. The reaction mixture was partitioned between EtOAc - 15 ml 5% $NaHCO_3$ - brine. The layers were separated and the EtOAc layer washed with brine, dried over $MgSO_4$ and evaporated under vacuum.

The crude product was chromatographed over 150 g silica gel, eluting with 60% EtOAc - 40% SSB. Fractions of 20 ml were collected, analyzing them by TLC. Fractions 47–75 contained the pure product and were combined and evaporated under vacuum, leaving 680 mg of the title product as a solid residue, 65% yield.

TLC: 60% EtOAc - 40% SSB; silica gel. $R_f$, 0.53.

IR: OH - 3316.8; 3223.3; C=O 1739.0. NMR: $CDCL_3$, δ) 0.7–1.0 (t, 3H); 2.4 (s, 3H); 1.1–3.2 (m, 18H); 3.3–3.6 (broad, 1H); 3.6 (s, 3H); 3.6–3.9 (broad, 2H); 3.9–4.2 (broad, 1H); 4.25–4.6 (q, 1H); 5.6–5.75 (m, 2H); 5.75 (s, 1H); 7.2–7.6 (q, 4H).

EXAMPLE 17

$\Delta^{6,8}$-Prostaglandin $I_1$,6,9-[[4-(dimethylamino)phenyl]imino]-6,9-deepoxy, methyl ester (a) A 1.0 g (1.64 mM) quantity of 6-keto-$PGF_{1\alpha}$-11,15-bis-dimethyl-t-butylsilyl ether, methyl ester, 1 ml MeOH, 418 mg (2 mM) N,N-dimethyl-p-phenylene diamine dihydrochloride and 490 ml (3.5 mM) triethylamine were stirred in the presence of 250 mg $MgSO_4$ under $N_2$ at room temperature in the dark for 21 hours. The reaction mixture was filtered, washing the solid with EtOAc. The filtrate was evaporated under vacuum. The crude product was chromatographed over 100 g silica gel, eluting with 10% EtOAc - 90% SSB. Fractions of 20 ml were collected, analyzing them by TLC. The product, $\Delta^{6,8}$-prostaglandin $I_1$, 6,9-[[4-(dimethylamino)phenyl]-imino]-6,9-deepoxy, methyl ester, 11,15-bis-dimethyl-t-butylsilyl ether, was found in fractions 31–64, which upon combining and evaporating under vacuum left 690 mg, 59% yield.

TLC: 20% EtOAc - 80% SSB; silica gel. $R_f$, 0.80.

NMR: ($CCl_4$, δ) 0.1 (2s, 12H); 0.4–1.1 (2 s +m, 21H); 1.1–1.9 (m, 12H); 2.0–3.7 (m, 7H); 3.0 (s, 6H); 3.6 (s, 3H), 3.9–4.3 (m, 1H); 4.3–4.6 (m, 1H); 5.4–5.8 (s+m, 3H); 6.7 (d. 2H); 7.1 (d, 2H).

(b) A 690 mg (0.97 mM) quantity of the silyl ether from (a) above, 3 ml THF and 1.23 g (3.9 mM) tetra-n-butylammonium fluoride were stirred at room temperature in the dark under $N_2$ for 66 hours. The reaction mixture was partitioned between EtOAc-brine. The layers were separated and the aqueous layer reextracted with EtOAc. The organic layers were dried over $MgSO_4$, filtered, and evaporated under vacuum. The crude product was chromatographed over 80 g silica gel, eluting with 80% EtOAc - 20% SSB. Fractions of 20 ml were collected, analyzing them by TLC. The title product was found in fractions 19–22 which upon combining and evaporating under vacuum weighed 300 mg, 64% yield.

TLC: 80% EtOAc - 20% SSB; silica gel. $R_f$, 0.62.

IR: OH - 3246.5, 3253.2, 3343.0; C=O 1738.0.

NMR: ($CDCl_3$, δ) 0.67–1.06 (m, 3H); 1.06–1.74 (m, 12H); 1.98–3.80 (m, 9H); 2.97 (s, 6H); 3.61 (s, 3H); 3.88–4.23 (m, 1H); 4.23–4.62 (m, 1H); 5.48–5.98 (s+m, 3H); 6.74 (d, 2H); 7.11 (d, 2H).

EXAMPLE 18

$\Delta^{6,8}$-Prostaglandin $I_1$, 6,9-[(m-aminophenyl)imino]-6,9-deepoxy, methyl ester (a) A 1.0 g (1.64 mM) quantity of 6-keto-$PGF_{1\alpha}$-11,15-bis-dimethyl-t-butylsilyl methyl ester, 354 mg (3.28 mM) m-phenylenediamine, 2 ml MeOH, a small crystal of pyridine.HCl and 250 mg $MgSO_4$ were stirred at room temperature under $N_2$ in the dark for 18 hours. The reaction mixture was filtered, washing the solid with EtOAc. The filtrate and wash were evaporated under vacuum and the crude product chromatographed over 100 g silica gel, eluting with 20% EtOAc - 80% SSB. Fractions of 20 ml were collected, analyzing them by TLC. Fractions 36–70 gave $\Delta^{6,8}$-prostaglandin $I_1$, 6,9-[(m-aminophenyl)imino]-6,9-deepoxy-, methyl ester-11,15-bis-dimethyl-t-butylsilyl ether, which upon combining and evaporating under vacuum left 1.23 g, 100% yield.

TLC: 20% EtOAc - 80% SSB, silica gel. $R_f$, 0.47.

NMR: ($CCl_4$, δ) 0.0 (d, 12H); 0.8 (s, 21H); 1.0–3.1 (m, 18H); 3.2–3.4 (m, 1H); 3.45 (s, 3H); 3.5–3.7 (broad, 2H); 3.8–4.2 (broad, 1H); 4.2–4.5 (q, 1H); 5.5–5.7 (m, 3H); 6.3–6.6 (m, 3H); 6.9–7.2 t, 1H).

(b) A 1.23 g (1.8 mM) quantity of the silyl ether from (a) above, 5 ml THF and 2.26 g tetra-n-butylammonium fluoride (7.2 mM) were stirred at room temperature under $N_2$ in the dark for 2 days. The reaction mixture was partitioned between EtOAc-brine. The layers were separated and the aqueous layer reextracted with EtOAc. The organic layers were dried over $MgSO_4$, filtered and evaporated under vacuum.

The crude product was chromatographed over 100 g silica gel, eluting with 80% EtOAc - 20% SSB. Fractions of 20 ml were collected, analyzing them by TLC. The pure product was found in fractions 34–80, which upon combining and evaporating weighed 410 mg, 50% yield.

TLC: 80% EtOAc - 20% SSB; silica gel. $R_f$, 0.64.

IR: NH/OH - 3350; C=O 1735.

NMR: ($CDCl_3$, δ) 0.8–1.0 (t, 3H); 1.1–3.2 (19H); 3.3–3.6 (broad, 1H); 3.6 (s, 3H); 3.6–4.0 (broad, 3H); 3.9–4.2 (broad, 1H); 4.2–4.6 (q, 1H); 5.5–5.7 (m, 2H); 5.7 (s, 1H); 6.4–6.7 (m, 3H); 7.0–7.3 (m, 1H).

EXAMPLE 19

$\Delta^{6,8}$-Prostaglandin $I_1$, 6,9-[[m-(dimethylamino)phenyl]-imino]-6,9-deepoxy-, methyl ester (a) A 1.0 g (1.64 mM) quantity of 6-keto-PGF$_{1\alpha}$-11,15-bis-dimethyl-t-butylsilyl ether, methyl ester, 1 ml MeOH, 418 mg (2 mM) N,N-dimethyl-m-phenylene diamine dihydrochloride, 490 ml (3.5 mM) N Et$_3$ and 250 mg MgSO$_4$ was stirred at room temperature at room temperature under N$_2$ in the dark for 24 hours. The reaction mixture was filtered, washing the solid with EtOAc. The filtrate was evaporated under vacuum. The crude product was chromatographed over 100 silica gel, eluting with 10% EtOAc - 90% SSB. Fractions of 20 ml were collected, analyzing them by TLC. The product, $\Delta^{6,8}$-prostaglandin $I_1$, 6,9-[[m-(dimethylamino)phenyl]imino]-6,9-deepoxy-, methyl ester-11,15-bis-dimethyl-t-butylsilyl ether, was found in fractions 21-40, which upon combining and evaporation under vacuum weighed 570 mg, 49% yield.

TLC: 10% EtOAc - 90% SSB. silica gel. R$_f$, 0.53.

NMR: (CCl$_4$, $\delta$) 0.1 (2s, 12H); 0.6-1.1 (s+m, 20H); 1.1-2.0 (m, 13H); 2.0-3.7 (m, 7H); 3.0 (s, 6H); 3.5 (s, 3H); 3.9-4.3 (m, 1H); 4.3-4.7 (m, 1H); 5.4-5.9 (m, 3H); 6.4-6.8 (m, 3H); 7.1-7.4 (m, 1H).

(b) A 570 mg (0.80 mM) quantity of the silyl ether from (a) above, 3ml THF and 1.10 g (3.5 mM) tetra-n-butylammonium fluoride was stirred at room temperature under N$_2$ in the dark for 3 days. The reaction mixture was partitioned between EtOAc-brine. The layers were separated and the aqueous layer reextracted with EtOAc. The organic layers were dried over MgSO$_4$, filtered and evaporated under vacuum.

The crude product was chromatographed over 70 g silica gel, eluting with 70% EtOAc - 30% SSB. Fractions of 20 ml were collected, analyzing them by TLC. The title product was found in fractions 31-52, which upon combining and evaporating under vacuum weighed 170 mg, 44% yield.

TLC: 80% EtOAc - 20% SSB; silica gel. R$_f$, 0.57.

IR: C=O 1742.7; OH - 3383.5, 3305.3.

NMR: (CDCl$_3$, $\delta$) 0.6-0.98 (m, 3H); 0.98-1.80 (m, 12H); 1.90-2.29 (m, 2H); 2.29-3.78 (m, 7H); 2.88 (s, 6H); 3.53 (s, 3H); 3.83-4.18 (m, 1H); 4.18-4.57 (m, 1H); 5.40-5.90 ((s+m, 3H); 6.30-6.83 (m, 3H); 7.04-7.40 (m, 1H).

EXAMPLE 20

$\Delta^{6,8}$-Prostaglandin $I_1$, 6,9-[[4-(ethoxy)phenyl]imino]-6,9-deepoxy-, methyl ester (a) A 1.0 g (1.64 mM) quantity of 6-keto-PGF$_{1\alpha}$-11,15-bis-dimethyl-t-butylsilyl ether, methyl ester, 249 mg (2.0 mM) m-phenetidine, a small crystal of pyridine hydrochloride, 1 ml methanol and 250 mg magnesium sulfate were stirred at room temperature under nitrogen in the dark for 18 hours. The reaction mixture was filtered, washing the solid with EtOAc. The filtrate was evaporated to dryness under vacuum. The residue was chromatographed over 120 g silica gel, eluting with 10% EtOAc - 90% SSB. Fractions of 20 ml were collected, analyzing them by TLC. Fractions 10-23 were combined and evaporated to give $\Delta^{6,8}$-prostaglandin $I_1$, 6,9-[[4-(ethoxy)phenyl]imino]-6,9-deepoxy-, methyl ester, 11,15-bis-dimethyl-t-butylsilyl ether.

TLC: 10% EtOAc - 90% SSB. silica gel. R$_f$, 0.17.

NMR: (CCl$_4$, $\delta$) 0.0 (d, 12H); 0.9 (s, 21H); 1.1-3.1 (m, 17H); 1.3-1.5 (t, 3H); 3.3-3.5 (m, 2H); 3.5 (s, 3H); 3.8-4.2 (q, 2H); 3.8-4.2 (broad, 1H); 4.3-4.5 (q, 1H); 5.5-5.7 (m, 3H); 6.6-6.9 (m, 3H); 7.1-7.4 (m, 1H).

(b) A 580 mg (0.82 mM) quantity of the silyl ether from (a) above, (3.4 mM) tetra-n-butylammonium fluoride and 5 ml THF were stirred at 0° C. under nitrogen in the dark for 2 hours and at room temperature for one day. It was then stored in the freezer for 9 days and again reacted at room temperature for one day. The reaction mixture was partitioned between EtOAc-brine. The layers were separated and the aqueous layer reextracted with EtOAc. The organic layers were dried over MgSO$_4$, filtered, and evaporated under vacuum.

The crude product was chromatographed over 60 g silica gel, eluting with 60% EtOAc - 40% SSB. Fractions of 20 ml were collected, analyzing them by TLC. Product was found in fractions 18-36, which upon combining and evaporating weighed 360 mg, 91% yield.

TLC: 70% EtOAc - 30% SSB, silica gel. R$_f$ of product, 0.56.

IR: 3350 - OH; 1740 C=O.

NMR: (CDCl$_3$, $\delta$) 0.8-1.0 (t, 3H); 1.1-3.1 (m, 19H); 1.3-1.5 (t, 3H); 3.2-3.5 (broad, 2H); 3.6 (s, 3H); 3.9-4.2 (q, 2H); 3.9-4.2 (broad, 1H); 4.3-4.6 (q, 1H); 5.6-5.7 (m, 2H); 5.8 (s, 1H); 6.7-6.9 (m, 3H); 7.2-7.5 (t, 1H).

EXAMPLE 21

$\Delta^{6,8}$-Prostaglandin $I_1$, 6,9-deepoxy-6,9-[(m-acetylthisphenyl)imino]-, methyl ester (a) A 1.0 g (1.64 mM) quantity of 6-keto-PGF$_{1\alpha}$-11,15-bis-dimethyl-t-butylsilyl ether, methyl ester, 410 mg (3.28 mM) 3-aminothiophenol, a small crystal of pyridine.HCl, 1 ml MeOH and 250 mg MgSO$_4$ were stirred at room temperature under N$_2$ in the dark for 23 hours. The reaction mixture was filtered, washing solid with EtOAc. The filtrate was evaporated under vacuum. Then the crude product was chromatographed over 100 g silica gel, eluting with 10% EtOAc - 90% SSB. Fractions of 20 ml were collected, analyzing them by TLC. $\Delta^{6,8}$-Prostaglandin $I_1$, 6,9-deepoxy-6,9-[(m-mercaptophenyl)imino]-, methyl ester, 11,15-bis-dimethyl-t-butylsilyl ether was found in fractions 16-28, which upon combining and evaporation weighed 0.09 g, 79% yield.

TLC: 10%EtOAc - 90% SSB; silica gel. R$_f$, 0.51.

NMR: (CCl$_4$, $\delta$) 0.1 (2s, 12H); 0.7-1.2 (s+m, 19H); 1.2-2.1 (m, 14H), 2.1-3.9 (m, 8H); 3.6 (s, 3H); 4.0-4.3 (m, 1H); 4.3-4.7 (m, 1H); 5.5-6.1 (s+m, 3H); 6.9-7.8 (m, 3H).

(b) An 860 mg (1.23 mM) quantity of the thiol from (a) above, 2 ml pyridine and 0.4 ml acetic achydrie were stirred at room temperature under N$_2$ in the dark for 30 minutes, when TLC showed the reaction tobe complete. Then a drop of water was added and the reaction mixture was stirred of 15 minutes. The reaction mixture was diluted with EtOAc and washed with 1N HCl, 5% NaHCO$_3$ and brine. The organic phase was then dried over Na$_2$SO$_4$ and evaporated under vacuum.

The crude product was combined with the crue product of another run (300 mg starting thiophenol) and was chromatographed over 100 g silica gel, eluting with 10% EtOAc - 90% SSB. Fractions of 20 ml were collected, analyzing them by TLC. The product, $\Delta^{6,8}$-prostaglandin $I_1$, 6,9-deepoxy-[(m-acetylthisphenyl)imino]-, methyl ester, 11,15-bis-dimethyl-t-butylsilyl ether, was found in fractions 29-47 and upon combining and evaporating weighed 690 mg, 56% yield.

TLC: 10% EtOAc - 90% SSB; silica gel. $R_f$, 0.49.

NMR: (CCl$_4$, δ) 0.1 (s), 0.6–1.2 (s+m), 1.2–1.9 (m); 1.9–3.2 (m); 2.4 (s); 3.3–3.8 (m); 3.6 (s); 3.9–4.5 (m); 4.5–4.7 (m); 5.4–6.0 (s +m), 6.8–7.7 (m).

(c) A 490 mg (0.66 mM) quantity of the silyl ether from (b) above was stirred at room temperature under N$_2$ in the dark in 24 ml isopropanol, 3 ml H$_2$O and 3 ml 1N HCl for 5 hours. The reaction mixture was diluted with EtOAc and washed with 5% NaHCO$_3$ and brine. The organic layer was dried over Na$_2$SO$_4$ and evaporated. The crude product was chromatographed over 50 g silica gel, eluting with 60% EtOAc - 40% SSB. Fractions of 20 ml were collected, analyzing them by TLC. Fractions 14–40 contained the product and were combined and evaporated. The residue weighed 90 mg, 27% yield.

TLC: 60% EtOAc - 40% SSB; silica gel. $R_f$, 0.53.

NMR: (CCl$_4$, δ) 0.63–1.09 (m, 3H); 1.09–1.8 (m, 12H); 1.8–3.2 (s +m, 9H); 3.2–4.6 (s +m, 8H); 5.41–5.87 (s +m, 3H); 7.0–7.7 (m, 4H).

EXAMPLE 22

(a)
2-Decarboxy-2-hydroxymethyl-6,9-deepoxy-6,9-[3-methylthio)-phenyl)-imino]-Δ$^{6,8}$-Prostaglandin I$_1$, 11,15-bis(t-butyldimethylsilyl ether)

A solution of 0.314 g (0.44 mM) of ester, 6,9-deepoxy-6,9-[3-(methylthio)phenyl)imino]-Δ$^{6,8}$-Prostaglandin I$_1$, monomethyl ester, 11,15-bis-dimethyl-t-butylsilyl ether in 3 ml of toluene was cooled under argon in a dry ice/acetone bath and treated dropwise with 0.69 ml (1.1 mM) of 25% diisobutylaluminum hydride in toluene. After one hour, 0.4 ml (0.6 mM) more of 25% diisobutylaluminium hydride in toluene was added, and after another hour the reaction was warmed to 0° C. and again 0.4 ml (0.6 mM) of the aluminum hydride reagent was added. Thirty minutes later the reaction appeared complete by TLC. It was then quenched with 0.5 ml of water, and stirred in the presence of air at 0° C. to room temperature overnight. After diluting with ethyl acetate and filtering through Celatom (diatomaceous earth), the reaction was washed twice with brine. The aqueous layers were reextracecd with ethyl acetate. The combined organic solutions were dried over anhydrous sodium sulfate and evaporated to give 280 mg of oil. Purification was accomplished by column chromatography on 30 g of silica gel 60 with a (20–80) ethyl acetate-hexane eluant. Fractions of 15 ml were collected. The colorless oily product was found in fractions 10–16. A 43% yield (129 mg) was obtained.

NMR: (CDCl$_3$, TMS) δ0.1 (s, 12H); 0.6–1.1 (2 s+m, 21H); 1.1–1.84 (m, 15H); 2.30–3.13 (s+m, 7H); 3.33–3.78 (m, 3H); 3.94–4.34 (m, 1H); 4.34–4.77 (m, 1H); 5.50–6.00 (s+m, 3H); 6.93–7.54 (m, 4H).

IR (film): 3340, 2920, 2850, 1585, 1480, 1360, 1250, 1070, 970, 840, 780 cm$^{-1}$.

TLC: 20% EtOAc - 80% SSB; silica gel. $R_f$, 0.25.

(b)
2-Decarboxy-2-hydroxymethyl-6,9-deepoxy-6,9-[3-(methylthio)-phenyl)-imino]-Δ$^{6,8}$-Prostaglandin I$_1$ A 129 mg (0.19 mM) quantity of the alcohol from (a) above, 2 ml of THF, and 0.223 g (0.71 mM) of tetra-n-butylammonium fluoride trihydrate were combined in a flask under argon. The mixture was stirred in the dark at room temperature for 46 hours, diluted with EtOAc, and washed twice with brine. The aqueous layers were reextracted. Drying (sodium sulfate) and evaporation of the combined EtOAc solutions left 0.23 g of brown oil. Column chromatography was done on 20 g of silica gel 60 which had been sonicated with nitrogen purged solvent. The eluant was 50% acetone - 50% hexane and 5-10 ml fractions were collected. The desired product, a dark gold waxy solid, was contained in fractions 9–16. A yield of 73% (62.8 mg) was obtained.

NMR (CDCl$_3$, TMS): δ0.7–1.11 (m, 3H); 1.11–1.80 (m, 14H); 1.94–3.23 (s+m, 10H); 3.31–3.80 (m, 3H), 3.94–4.29 (m, 1H); 4.29–4.72 (m, 1H); 5.61–6.00 (s+m, 3H); 6.90–7.68 (m, 4H).

IR (film): 3320, 2915, 2850, 1585, 1480, 1060, 970, 790, 700 cm$^{-1}$.

TLC: 50% acetone - 50% hexane; silica gel. $R_f$, 0.36.

EXAMPLE 23

(a)
6,9-Deepoxy-6,9-(3-methylthiophenylimino)-Δ$^{6,8}$-prostaglandin I$_1$, monomethylamide, bis(t-butyldimethylsilyl ether)

A 0.216 g (0.31 mM) quantity of acid, 6,9-deepoxy-6,9-[3-((methylthio)phenyl)imino]-Δ$^{6,8}$-prostaglandin I$_1$, 11,15-bis-dimethyl-t-butylsilyl ether, dissolved in 3 ml of THF under argon was treated with 85 μl (0.61 mM) of triethylamine and 60 μl (0.62 mM) of isobutyl chloroformate. After stirring in the dark at room temperature for 130 minutes, 0.9 ml of condensed monomethylamine was allowed to bubble into the reaction. The mixture was stirred in the dark at room temperature for 17 hours, diluted with methylene chloride and water, and washed with 1N HCl, 5% sodium bicarbonate, and brine. Drying (sodium sulfate) and evaporation gave 0.3 g of brown oil. The oil was chromatographed on 20 g of silica gel 60 eluting with 50% EtOAc - 50% hexane, collecting 10 ml fractions.

Fractions 9–20 contained 0.178 g (81% yield) of the title compound as a waxy light yellow solid.

NMR: (CDCl$_3$, TMS) δ0.1 (s, 12H); 0.7–1.13 (2 s+m, 20H); 1.13–1.9 (m, 13H); 1.9–2.27 (m, 2H); 2.3–3.12 (s+m, 10H); 3.38–3.66 (m, 1H); 3.95–4.3 (m, 1H); 4.3–4.67 (m, 1H); 5.45–6.0 (m, 4H); 6.92–7.6 (m, 4H).

IR (film): 3230, 3055, 2915, 2850, 1690, 1580, 1480, 1360, 1250, 1080, 835, 775 cm$^{-1}$.

TLC- 50% EtOAc - 50% SSB; silica gel. $R_f$, 0.38.

(b)
6,9-Deepoxy-6,9-(3-methylthiophenylimino)-Δ$^{6,8}$-prostaglandin I$_1$, monomethyl amide A solution of 0.18 g (0.25 mM) of the amide from (a) above in 2.3 ml of THF was charged with 0.261 g (0.83 mM) of tetra-n-butylammonium fluoride trihydrate. The mixture was stirred under argon in the dark at room temperature for 53 hours. The reaction was diluted with EtOAc and washed twice with brine, reextracting the aqueous layers. The combined organic layers were dried (sodium sulfate) and concentrated in vacuo. The resulting oil was chromatographed on 20 g of silica gel 60 which had been sonicated with nitrogen purged solvent. Elution was done with 40% acetone - 60% methylene chloride and 60% acetone - 40% methylene chloride, and 10 ml fractions were collected. The product, a tan sticky solid, was isolated from fractions 13–31 by solvent removal. A 77% yield (92% mg) was realized.

NMR: (CDCl$_3$, TMS) δ0.68–1.09 (m, 3H); 1.09–1.87 (m, 12H); 1.87–2.22 (m, 2H); 2.22–3.76 (m+s+d, 13H); 3.94–4.30 (m, 1H); 4.30–4.68 (m, 1H); 5.48–6.12 (m, 4H); 6.90–7.61 (m, 4H).

IR (film): 3270, 2915, 2850, 1640, 1585, 1480, 1060, 970, 910, 790, 735 cm$^{-1}$.

TLC: 40% acetone - 60% methylene chloride; silica gel. R$_f$, 0.26.

EXAMPLE 24

2-Decarboxy-2-chloromethyl-6,9-deepoxy-6,9-[3-(methylthio)-phenyl]-imino-Δ$^{6,8}$-prostaglandin I$_1$, bis(t-butyldimethylsilyl ether)

Dichlorotriphenylphosphorane was prepared by refluxing 0.38 g (1.46 mMO of triphenylphonphine, 0.347 g (1.46 mM) of hexachloroethane and 14 ml of dry distilled acetonitrile in a dry flask under argon for one hour. After cooling the solvent was removed in vacuo. The oily residue was treated with 0.491 g (0.72 mM) of the alcohol of Example 22(a) dissolved in 15 ml of dry distilled THF. The reaction was stirred 20 minutes at room temperature and poured into water/methylene chloride. The water layer was extracted with more methylene chloride, and the combined lower layers were washed with brine (3 times), 5% sodium bicarbonate, and brine. Drying (sodium sulfate) and concentration afforded 0.91 g of tan solid. The material was chromatographed on 30 g of silica gel 60, eluting with 15% EtOAc - 85% hexane, taking 15 ml fractions. A yellow oil weighing 0.50 g (99% yield) was obtained from fractions 3–5.

NMR: (CDCl$_3$, TMS) δ0.1 (s, 12H); 0.67–1.10 (2 s+m, 19H); 1.10–1.94 (m, 16H); 2.30–3.14 (s+m, 7H); 3.30–3.74 (m, 3H); 3.90–4.30 (m, 1H); 4.30–4.72 (m, 1H); 5.58–6.00 (s+m, 3H); 6.90–7.55 (m, 4H).

IR (film): 2930, 2850, 1585, 1480, 1360, 1255, 1080, 965, 838, 777 cm$^{-1}$.

TLC: 50% toluene - 50% SSB; silica gel. R$_f$, 0.58.

EXAMPLE 25

(a)
9-Deepoxy-6,9-[[m-(methylthio)phenyl]imino]-PGI$_1$, bis-t-butyldimethylsilyl ether A 1.02 g (1.43 mM) quantity of 6,9-deepoxy-6,9-[3-((methylthio)-phenyl)imino]-Δ$^{6,8}$-prostaglandin I$_2$, methyl ester, 11,15-bis-dimethyl-t-butyl silyl ether was dissolved in 10 ml of methanol and 10 ml of THF. The solution was treated with 3 ml of N NaOH and stirred at 25° for 19 hr. The reaction was then diluted with methylene chloride and 1 NHCl. The aqueous layer was separated and re-extracted with methylene chloride. The combined methylene chloride solutions were washed with saturated brine, dried over magnesium sulfate, and filtered. The filtrate was concentrated under vacuum leaving 0.97 g of the title product.

NMR: (CDCl$_3$, TMS) δ0.05–0.15 (M, 12 H); 0.65–1.1 (m, 21H); 1.0–2.0 (m, 12H); 2.05–3.1 (m, 6); 2.50 (s, 3H); 3.3–3.6 (m, 1H); 3.95–4.3 (m, 1H); 4.3–4.7 (bq, 1H); 5.6–5.95 (m, 3H); 6.9–7.55 (m, 4H).

TLC: 10% ethyl acetate - 90% SSB (plate pre-dipped in (5-95) acetate acid-methylene chloride and then air dried); silica gel. R$_f$, 0.65.

(b)
9-Deepoxy-6,9-[[m-(methylthio)phenyl]imino]-PGI$^1$, N,N-dimethyl amide, 11,15-bis-t-butyldimethylsilyl ether A 200 mg (0.29 mM) quantity of the acid from (a) above was dissolved in 3 ml of the THF and the solution treated with 120 μl (87 mg, 0.85 mM) of triethylamine and 41 μl (43 mg, 0.32 mM) of isobutyl chloroformate. The mixture was stirred at 25° for 30 minutes and then treated with 45 mg (0.55 mM) of dimethylamine hydrochloride. After 17 hours the reaction was partitioned between ether and 5% aqueous sodium bicarbonate solution. The ether layer was separated, washed with 1N HCl and dried over magnesium sulfate. Concentration of the solvent under vacuum left 142 mg of crude product. This was chromatographed over a size B E. Merk Lobar silica gel column eluted with 40%/60% ethyl acetate-n-hexane. Twelve ml fractions were collected. The title product was found by TLC to be in fractions 29 to 39. Concentration of these fractions left 96 mg of product.

NMR: (CDCl$_3$, TMS) w 0.05–0.15 (m, 12H); 0.65–1.1 (m, 21H); 1.15–1.8 (m, 12H); 2.1–3.1 (M, 6H); 2.50 (s, 3H); 2.92 (s, 3H); 2.97 (s, 3H); 3.4–3.6 (m, 1H); 3.95–4.3 (m, 1H); 4.3–4.6 (m, 1H); 5.6–5.95 (m, 3H); 6.9–7.5 (m, 4H).

TLC: 40% EtOAc - 60% SSB; silica gel. R$_f$, 0.39.

(c) 9-Deepoxy-6,9[[m-methylthio)phenyl]imino]-PGI$_1$, N,N-dimethyl amide

A 96 mg (0.14 mM) quantity of bis-t-butyl dimethylsilyl ether dimethyl amide of (b) above as dissolved in 1 ml of dry THF and the solution treated with 161 mg (0.51 mM) of tetrabutylammonium fluoride trihydrate. After 70 hours the reaction was concentrated under vacuum and the residue added to the top of a 5 g silica gel 60 column. The column was eluted with 40% acetone : 60% methylene chloride, collecting 2 ml fractions. The product was found by TLC in fractions 11–16. Concentration of these fractions under vacuum left 46 mg of product.

NMR: (CDCl$_3$, TMS) w 0.7–1.05 (m, 3H); 1.05–1.85 (m, 12H); 1.95–3.2 (m, 8H); 2.52 (s, 3H); 2.93 (s, 3H); 2.97 (s, 3H); 3.2–3.6 (m, 1H); 3.9–4.25 (m, 1H); 4.3–4.7 (m, 1H); 5.6–5.95 (m, 3H); 6.85–7.6 (m, 4H).

TLC: R$_f$, 0.26 in ethyl acetate; R$_f$, 0.46 in 40% acetone - 60% methylene chloride; silica gel.

EXAMPLE 26

(a)
9-Deepoxy-6,9-[[m-(methylthio)phenyl]imino]-PGI$_1$, amide, bist-t-butyldimethylsilyl ether A 203 mg (0.29 mM) quantity of bis-t-butyldimethylsilyl ether, acid from Example 25(a) was dissolved in 3 ml of dry THF and the solution was treated with 81 μl (59 mg, 0.58 mM) of triethylamine and 57 μl (60 mg, 0.44 mM) of isobutylchloroformate. After the reaction was stirred 2 hours at 25°, 1 ml of liquid ammonia was allowed to evaporate and was bubbled through the reaction mixture. The reaction was then stirred an additional 22 hours, after which it was poured into methylene chloride and water. The methylene chloride layer was separated and was washed with 1 N HCl, 5% aqueous sodium bicarbonate solution, and dried over magnesium sulfate. Concentration of the filtered solution under vacuum left 230 mg of crystalline solid. This was chromatographed over 10 g of silica gel 60 eluting with 65%/35% ethyl acetate-n-hexane. Five ml fractions were collected. The product was found by TLC in fractions 9-20. Concentrations of these fractions under vacuum left 150 mg of the title product.

TLC: 65%/35% ethyl acetate-n-hexane; silica gel. $R_f$, 0.27.

(b) 9-Deepoxy-6,9-[[m-(methylthio)phenyl]imino]-PGI$_1$, amide

A 150 mg (0.21 mM) quantity of the amide from (a) above was dissolved in 2 ml of dry THF and the solution treated with 225 mg (0.71 nM) of tetra-n-butyl ammonium fluoride trihydrate. After stirring 3 days at 25°, the reaction was concentrated under vacuum and the residue chromatographed over 10 g of silica gel 60. The column was eluted with 50% acetone - 50% methylene chloride, collecting 5 ml fractions. The product was found by TLC in fractions 9-24. Concentration of these fractions under vacuum left 69 mg of product.

NMR: (CDCl$_3$, TMS) w 0.7-1.1 (m, 3H); 1.1-1.9 (m, 12H); 1.95-2.3 (m, 2H); 2.3-3.15 (m, 6H); 2.50 (s, 3H); 3.3-3.7 (m, 1H); 3.9-4.3 (m, 1H); 4.3-4.7 (m, 1H); 5.6-6.1 (m, 5H); 6.9-7.55 (m, 4H).

TLC: 50% acetone - 50% methylene chloride; silica gel. $R_f$, 0.30.

EXAMPLE 27

(a) 9-Deepoxy-6,9-[[m-(methylthio)phenyl]imino]-PGI$_1$, bis-t-butyl dimethylsilyl ether, n-heptyl amine A 184 mg (0.26 mM) quantity of bis-t-butyl dimethylsilyl ether, acid from Example 25(a) was dissolved in 3 ml of dry THF and the solution treated with 120 μl (87 mg, 0.85 mM) of the triethylamine and 41 μl (43 mg, 0.32 mM) of isobutylchloroformate. The mixture was stirred for 30 minutes at 25° under an Ar atmosphere and then treated with 78 μl (60.25 mg. 0.53 mM) of n-heptyl amine. After 17 hours the reaction was poured into methylene chloride and extracted with 1N and HCl and 5% aqueous sodium bicarbonate solution. The methylene chloride layer was then dried over magnesium sulfate, filtered, and concentrated under vacuum leaving 210 mg of crude product. This was chromatographed over an E. Merck Lobar size B silica gel 60 column eluted with 30%/70% ethyl acetate-n-hexane. Twelve ml fractions were collected. The product was found by TLC in fractions 19-25. Concentration of these fractions left 150 mg of product.

NMR: (CDCl$_3$, TMS) 0.05-0.15 (m, 12H); 0.5-1.05 (m, 24H); 1.05-1.85 (m, 22H); 1.85-2.3 (m, 2); 2.3-3.35 (m, 6H); 2.52 (s, 3H); 3.35-3.6 (m, 1H); 3.9-4.3 (m, 1H); 4.3-4.65 (m, 1H); 5.2-5.95 (m, 4H); 6.85-7.6 (m, 4H).

TLC: 20%/80% ethyl acetate-n-hexane; silica gel. $R_f$, 0.29.

(b) 9-Deepoxy-6,9-[[m-(methylthio)phenyl]imino]-PGI$_1$, n-heptyl, amide

A 150 mg (0.19 mM) quantity of bis-t-butyl dimethylsilyl ether, n-heptyl amide from (a) above, was dissolved in 2.0 ml of THF and the solution treated with 216 mg (0.69 mM) of tetra-n-butyl ammonium fluoride trihydrate. The reaction was then concentrated under vacuum and the residue chromatographed over 10 g of silica gel 60, eluting with 25% acetone - 75% methylene chloride. Five ml fractions were collected. The product was found by TLC in fractions 10-18. Concentration of these fractions under vacuum gave 96 mg of product.

NMR: (CDCl$_3$, TMS) w 0.65-1.1 (m, 6H); 1.1-1.85 (m, 22H), 1.85-2.25 (m, 2H); 2.3-3.35 (m, 8H); 2.50 (s, 3H); 3.35-3.7 (m, 1H); 3.9-4.25 (m, 1H); 4.25-4.7(m, 1H); 5.4-6.0 (m, 4H); 6.85-7.55 (m, 4H).

TLC: 25% acetone - 75% methylene chloride; silica gel. $R_f$, 0.37.

EXAMPLE 28

(a) 9-Deepoxy-6,9-[[o-(methylthio)phenyl]imino]-PGI$_1$, methyl ester, bis-t-butyldimethylsilyl ether A mixture of (3.27 mM) quantity of 6-keto-PGE$_1\alpha$ methyl ester, 11,15-bis-t-butyldimethylsilyl ether, a 0.46 g (3.30 mM) quantity of 2-methyl thioaniline, a crystal of pyridine hydrochloride and a 0.50 g quantity of anhydrous magnesium sulfate was added to 2 ml of methanol and was stirred at 25° under a N$_2$ atmoshere. After 24 hours the reaction was filtered and the solids washed with ethy acetate. The combined filtrates were concentrated under vacuum and the residue chromatographed over 150 g of silica gel 60, eluting with 10% EtOAc-90% SSB. Twenty ml fractions were collected. Fractions 13-26 were concentrated leaving 790 mg of material which contained the desired product.

(b) 9-Deepoxy-6,9-[[o-(methylthio) phenyl]imino]-PGI$_1$, methyl ester 1.06 g of the material from (a) above was dissolved in 48 ml of isopropanol, 6 ml of water and 6 ml of 1N HCl. The resultant solution was stirred in the dark at 25° for 7 hours. The reaction was then partitioned between ethyl acetate and 5% aqueous sodium bicarbonate. The ethyl acetate layer was washed with brine, dried over magnesium sulfate and filtered. Concentration of the ethyl acetate solution under vacuum left a residue as a dark oil which was chromatographed over 100 g of silica gel 60. The column was eluted vertically with 500 mol of (20-80), 500 ml of (30-70), 500 ml of (40-60), 500 ml of (50-50), 500 ml of (60-40), 500 ml of (70-30), and 500 ml of (80-20) EtOAc-SSB. Twenty ml fractions were collected. The title product was found by TLC in fractions 136-160. Concentration of these fractions under vacuum left 100 mg of the title product.

NMR: (CDCl$_3$, TMS) w 0.6-1.0 (m, 3H); 1.0-1.9 (m, 12H); 1.9-3.0 (m, 8H); 2.35 (s, 3H); 3.3-3.7 (m, 1H); 3.63 (s,3H); 3.8-4.2 (m, 1H); 4.2-4.6 (m, 1H); 5.4-5.9 (m, 3H); 7.0-7.6 (m, 4H).

TLC: 40% EtOAc-60% SSB; silica gel. $R_f$, 0.23.
IR (film): 3400, 1735 cm$^{-1}$.

I claim:

1. A compound of the formula

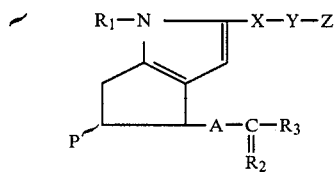

wherein Z is
(a) —CO$_2$R$_8$ wherein R$_8$ is a pharmaceutically acceptable metal cation, hydrogen, a straight or branched alkyl group having from 1 to 6 carbon atoms, phenyl, phenyl substituted in any position with from 1 to 3 substituents selected from chlorine or a straight or branched alkyl group having from 1 to 3 carbon atoms, or phenyl substituted in the para-position with —NHCOR$_{10}$, —COR$_{11}$, —OCOR$_{12}$, or —CH=NNHCONH$_2$ wherein R$_{10}$ is methyl, phenyl, acetamidophenyl, benzamidophenyl, or amino; R$_{11}$ is methyl, methoxy, phenyl or amino; and R$_{12}$ is phenyl or acetamidophenyl;

(b) —CONR$_{13}$R$_{14}$ wherein each of R$_{13}$ and R$_{14}$ is the same or different and is hydrogen, an alkyl group having from 1 to 8 carbon atoms, phenyl or benzyl;

(c) —CH$_2$OR$_5$ wherein R$_5$ is hydrogen, a straight or branched alkyl group having from 1 to 6 carbon atoms, benzoyl, a straight or branched alkanoyl group having from 2 to 5 carbon atoms, tetrahydropyranyl, trimethylsilyl, tert-butyldimethylsilyl, or

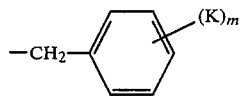

wherein K is a straight or branched alkyl group having from 1 to 6 carbon atoms, fluorine, chlorine, bromine, trifluoromethyl, a straight or branched alkoxy group having from 1 to 4 carbon atoms, phenyl, an alkanoyl group having from 2 to 5 carbon atoms, an alkanoylamido group having from 2 to 5 carbon atoms, nitro, or (i) —CO$_2$R$_8$ wherein R$_8$ has the meaning defined hereinabove;

(ii) —CH$_2$OR$_{19}$, —OR$_{19}$, or —SR$_{19}$ wherein R$_{19}$ is hydrogen, a straight or branched alkyl group having from 1 to 6 carbon atoms, an alkanoyl group having from 2 to 5 carbon atoms, benzoyl, benzyl, trimethylsilyl, tert-butyldimethylsilyl or tetrahydropyranyl; or (iii) —NR$_{20}$R$_{21}$ wherein each of R$_{20}$ and R$_{21}$ is the same or different and is hydrogen or an alkyl group having from 1 to 6 carbon atoms; and m is zero to 3 with the provisos that when K is phenyl, CO$_2$R$_8$ or —CH$_2$OR$_{19}$, m is 1, and when K is —OR$_{19}$ or —SR$_{19}$, m is 1 or 2; or

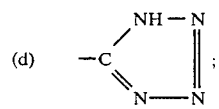

wherein Y is —CH$_2$CH$_2$—, cis- or trans—CH=CH—, or —CH$_2$CF$_2$;

wherein X is —(CH$_2$)$_n$ wherein n is 1 to 5;

wherein R$_1$ is hydrogen, a straight or branched alkyl group having from 1 to 6 carbon atoms, a cycloalkyl group having from 3 to 7 carbon atoms, a bicycloalkyl group having from 6 to 10 carbon atoms, or

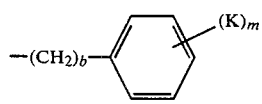

wherein b is zero or 1, and each of K and m has the meaning defined hereinabove;

wherein P is hydrogen, ~OR$_5$ or ~CH$_2$OR$_5$ wherein R$_5$ has the meaning defined hereinabove;

wherein A is —CH$_2$CH$_2$—, cis- or trans—CH=CH— or —C≡C—;

wherein R$_2$ is H,H; =O; α—R$_4$,β—R$_4$ wherein R$_4$ is hydrogen or an alkyl group having from 1 to 4 carbon atoms, and R$_5$ has the meaning defined hereinabove; and wherein R$_3$ is cis-2-pentenyl, —C(R$_6$)(R$_7$)—B—E or —C(R$_6$)(R$_7$)C$_q$H$_{2q}$CH$_3$ wherein B is a bond, oxa, or alkylene moiety having from 1 to 6 carbon atoms; E is

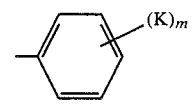

wherein each of K and m has the meaning defined hereinabove; q is 1 to 4; and each of R$_6$ and R$_7$ is hydrogen, fluorine or an alkyl group having from 1 to 4 carbon atoms with the provisos that when R$_5$ is fluorine, R$_7$ is either hydrogen or fluorine, and when B is oxa, each of R$_6$ and R$_7$ is other than fluorine; and pharmaceutically acceptable salts thereof with the further overall proviso that each compound is other than one formed when the substituent groups Z, X, Y, R$_1$, P, R$_2$ and R$_3$ have the following meanings:

wherein Z is (a) —CO$_2$R$_8$ wherein R$_8$ has the meaning defined hereinabove;

(b) —CONR$_{13}$R$_{14}$ wherein each of R$_{13}$ and R$_{14}$ is hydrogen, an alkyl group having from 1 to 6 carbon atoms, phenyl or benzyl;

(c) —CH$_2$OR$_5$ wherein R$_5$ is hydrogen, a straight or branched alkyl group having from 1 to 6 carbon atoms, benzoyl or an alkanoyl group having 2 carbon atoms;

wherein X is —(CH$_2$)$_n$ and n is 2 or 4;

wherein Y is —CH$_2$CH$_2$—; trans —CH=CH—; or —CH$_2$CF$_2$;

wherein R$_1$ is hydrogen, a straight or branched alkyl group having from 1 to 4 carbon atoms, a cycloalkyl group having from 3 to 7 carbon atoms or

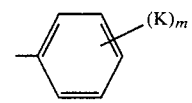

wherein K is a straight or branched alkyl group having from 1 to 3 carbon atoms, fluorine, chlorine, trifluoromethyl, an alkoxy group having 1 carbon atom, phenyl, —CO$_2$R$_8$ wherein R$_8$ has the meaning defined hereinabove, or —CH$_2$OR$_{19}$ wherein R$_{19}$ is hydrogen, a straight or branched alkyl group having from 1 to 6 carbon atoms, an alkanoyl group having 2 carbon atoms, or benzoyl; and m is zero to 3 with the proviso that when K is —CO$_2$R$_8$, —CO$_2$OR$_{19}$ or phenyl, m is 1;

wherein P is hydrogen, ~OR$_5$ or ~CH$_2$OR$_5$ and each R$_5$ is hydrogen;

wherein R$_2$ is H,H; =O; α—R$_4$,β—OR$_5$,β—R$_4$ wherein each R$_4$ is hydrogen or an alkyl group having from 1 to 3 carbon atoms; and each R$_5$ is hydrogen, an alkyl group having 1 carbon atom, or an alkanoyl group having 2 carbon atoms; and wherein R$_3$ has the meaning defined hereinabove except that K as used therein has the following meaning: a straight or branched alkyl group having from 1 to 3 carbon atoms, fluorine, chlorine, trifluoromethyl, an alkoxy group having 1 carbon atom, phenyl, —$CO_2R_8$ wherein $R_8$ has the meaning defined hereinabove, or —$CH_2OR_{19}$ wherein $R_{19}$ is hydrogen, a straight or branched alkyl group having from 1 to 6 carbon atoms, an alkanoyl group having 2 carbon atoms, or benzoyl.

2. A compound of claim 1 wherein $R_1$ is a cycloalkyl group having from 6 to 10 carbon atoms or the group

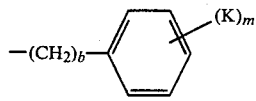

wherein b, K and m have the meanings defined in claim 1.

3. A compound of claim 2 wherein m is 0 to 2.

4. A compound of claim 3 which is
6,9-deepoxy-6,9-[(phenylmethyl)imino]-$\Delta^{6,8}$-prostaglandin $I_1$ methyl ester;
6,9-deepoxy-6,9-[p-ethoxyphenyl)imino]-$\Delta^{6,8}$-prostaglandin $I_1$ methyl ester;
6,9-deepoxy-6,9-[[m-(methylthio)phenyl]imino]-$\Delta^{6,8}$-prostaglandin $I_1$, methy ester;
6,9-deepoxy-6,9-[[m-(methylthio)phenyl]imino]-$\Delta^{6,8}$-prostaglandin $I_1$, sodium salt;
6,9-[[4-(dimethylamino)phenyl]imino]-6,9-deepoxy-$\Delta^{6,8}$prostaglandin $I_1$, methyl ester;
6,9-deepoxy-6,9-[(m-acetylthiophenyl)imino]-$\Delta^{6,8}$-prostaglandin $I_1$, methyl ester;
2-decarboxy-2-hydroxymethyl-6,9-deepoxy-6,9-[3-(methylthio)-phenyl)-imino-$\Delta^{6,8}$-prostaglandin $I_1$;
6,9-deepoxy-6,9-(3-methylthiophenylimino)-$\Delta^{6,8}$prostaglandin $I_1$, monomethyl amide;
9-deepoxy-6,9-[[m-methylthio)phenyl]imino-]-prostaglandin $I_1$, N, N-dimethyl amide; or
9-deepoxy-6,9-[[m-(methylthio)phenyl]imino]-prostaglandin $I_1$, amide.

5. A compound of claim 4 which is
6,9-deepoxy-6,9-[[m-(methylthio)phenyl]imino]-$\Delta^{6,8}$-prostaglandin $I_1$, methyl ester;
2-decarboxy-2-hydroxymethyl-6,9-deepoxy-6,9-[3-(methylthio)-phenyl)-imino]-$\Delta^{6,8}$-prostaglandin $I_1$; or
6,9-deepoxy-6,9-[(m-acetylthiophenyl)imino]-$\Delta^{6,8}$-prostaglandin $I_1$, methyl ester.

6. A compound of the formula

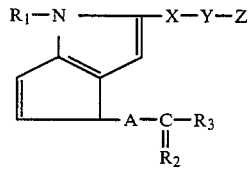

wherein Z is
(a) —$CO_2R_8$ wherein $R_8$ is a pharmaceutically acceptable metal cation, hydrogen, a straight or branched alkyl group having from 1 to 6 carbon atoms, phenyl, phenyl substituted in any position with from 1 to 3 substituents selected from chlorine or a straight or branched alkyl group having from 1 to 3 carbon atoms, or phenyl substituted in the para-position with —$NHCOR_{10}$, —$COR_{11}$, —$OCOR_{12}$, or —CH=$NNHCONH_2$ wherein $R_{10}$ is methyl, phenyl, acetamidophenyl, benzamidophenyl, or amino; $R_{11}$ is methyl, methoxy, phenyl or amino; and $R_{12}$ is phenyl or acetamidophenyl;

(b) —$CONR_{13}R_{14}$ wherein each of $R_{13}$ and $R_{14}$ is the same or different and is hydrogen, an alkyl group having from 1 to 6 carbon atoms, phenyl or benzyl;

(c) —$CH_2OR_5$ wherein $R_5$ is hydrogen, a straight or branched alkyl group having from 1 to 6 carbon atoms, benzoyl, a straight or branched alkanoyl group having from 2 to carbon atoms, tetrahydropyranyl, trimethylsilyl, tert-butyldimethylsily, or

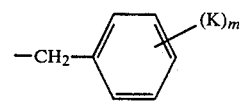

wherein K is a straight or branched alkyl group having from 1 to 6 carbon atoms, fluorine, chlorine, bromine, trifluoromethyl, a straight or branched alkoxy group having from 1 to 4 carbon atoms, phenyl, an aklanoy group having from 2 5 carbon atoms, an alkanoylamido group having from 2 to 5 carbon atoms, nitro, or (i) —$CO_2R_8$ wherein $R_8$ has the meaning defined hereinabove;

(ii) —$CH_2OR_{19}$, —$OR_{19}$, or —$SR_{19}$ wherein $R_{19}$ is hydrogen, a straight or branched alkyl group having from 1 to 6 carbon atoms, an alkanoyl group having from 2 to 5 carbon atoms, benzoyl, benzyl, trimethylsilyl, tert-butyldimethylsilyl or tetrahydropyranyl; or (iii) —$NR_{20}R_{21}$ wherein each of $R_{20}$ and $R_{21}$ is the same or different and is hydrogen or an alkyl group having from 1 to 6 carbon atoms; and m is zero to 3 with the provisos that when K is phenyl, —$CO_2R_8$ or —$CH_2OR_{19}$, m is 1, and when K is —$OR_{19}$ or —$SR_{19}$, m is 1 or 2; or (d) 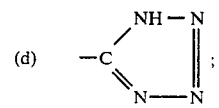 ;

wherein Y is —$CH_2CH_2$—, cis- or trans-CH=CH—, or —$CH_2CF_2$;

wherein X is —$(CH_2)_n$ wherein n is 1 to 5;

wherein $R_1$ is hydrogen, a straight or branched alkyl group having from 1 to 6 carbon atoms, a cycloalkyl group having from 3 to 7 carbon atoms, a bicycloalkyl group having from 6 to 10 carbon atoms, or

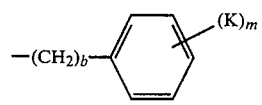

wherein b is zero or 1, and each of K and m has the meaning defined hereinabove;

wherein A is —$CH_2CH_2$—, cis- or trans-CH=CH— or —C≡C—;

wherein $R_2$ is H,H; =O; α—$R_4$, β—$OR_5$; or α—$OR_5$, β—$R_4$ wherein $R_4$ is hydrogen or an alkyl group having from 1 to 4 carbon atoms, and $R_5$ has the meaning defined hereinabove; and wherein $R_3$ is cis-2-pentenyl, —$C(R_6)(R_7)$—B—E or —$C(R_6)(R_7)C_qH_{2q}CH_3$ wherein B is a bond, oxa, or an alkylene moiety having from 1 to 6 carbon atoms;
E is

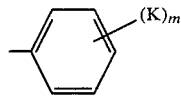

wherein each of K and m has the meaning defined hereinabove; q is 1 to 4; and each of $R_6$ and $R_7$ is hydrogen, fluorine or an alkyl group having from 1 to 4 carbon atoms with the provisos that when $R_6$ is fluorine, $R_7$ is either hydrogen or fluorine, and when B is oxa, each of $R_6$ and $R_7$ is other than fluorine; and pharmaceutically acceptable salts thereof.

7. A compound of claim 6 wherein X is —$CH_2CH_2$— or —$(CH_2)_4$—; Y is —$CH_2CH_2$— or —$CH_2CF_2$; Z is —$CO_2R_8$ wherein $R_8$ is hydrogen, a pharmacologically acceptable metal cation, or methyl; $R_1$ is hydrogen, a straight or branched alkyl group having from 1 4 carbon atoms, cyclohexyl or

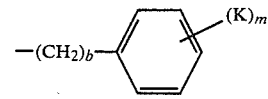

wherein m is zero to 2; $R_2$ is $\alpha$—$R_4$,$\beta$—$OR_5$; $\alpha$—$OR_5$,$\beta$—$R_4$; =O; or H,H wherein $R_4$ is hydrogen or methyl and $R_5$ is hydroxy; $R_3$ is (a) —$C(R_6)(R_7)C_qH_{2q}CH_3$ wherein $R_6$ and $R_7$ are the same and are fluoro or methyl; (b) —$C(R_6)(R_7)$—B—E wherein $R_6$ and $R_7$ are the same or different and are hydrogen or methyl and E is

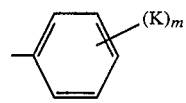

wherein m is zero to 2; or (c) cis-2-pentenyl.

8. A compound of claim 7 wherein K is fluoro, chloro, trifluoromethyl, or an alkoxy group having 1 or 2 carbon atoms.

9. A compound of claim 6 which is 6,9-deepoxy-10,11-didethydro-11-deoxy-6,9-[(p-nitrophenyl)imino]-$\Delta^{6,8}$-prostaglandin $I_1$, methyl ester.

10. A compound which is 2-decarboxy-2-chloromethyl-6,9-deepoxy-6,9-[3-(methylthio)phenyl]imino-$\Delta^{6,8}$-prostaglandin $I_1$.

* * * * *

UNITED STATES PATENT OFFICE
CERTIFICATE OF CORRECTION

Patent No. 4,496,742          Dated January 29, 1985

Inventor(s) Herman W. Smith

It is certified that error appears in the above-identified patent and that said Letters Patent are hereby corrected as shown below:

Column 5, line 4, "benzoyl having" should read -- benzoyl or alkanol having --.

Column 5, line 58, "-$CH_2OR_{19}$ is" should read -- $CH_2OR_{19}$ wherein $R_{19}$ is --.

Column 18, line 23, "PGI-hd 1" should read -- $PGI_1$ --.

Column 20, line 59, "6,9-[(acetamidophenyl)" should read -- 6,9-Deepoxy-6,9-[(acetamidophenyl) --.

Column 24, lines 5-6, "4H) cl EXAMPLE 14" should read -- 4H). EXAMPLE 14 --.

Column 28, line 30, "[(m-acetylthisphenyl)imino]-" should read -- [(m-acetylthiophenyl)imino]- --.

Column 28, line 67, "[(m-acetylthisphenyl)imino]-" should read -- [(m-acetylthiophenyl)imino]- --.

Column 36, line 3, "wherein $R_2$ is H,H; =O; $\alpha$-$R_4$,$\beta$-$R_4$" should read -- wherein $R_2$ is H,H; =O; $\alpha$-$R_4$,$\beta$-$OR_5$; or $\alpha$-$OR_5$,$\beta$-$R_4$ --.

Column 36, line 20, "$R_5$" should read -- $R_6$ --.

Column 36, line 62, "$R_2$ is H,H; =O; $\alpha$-$R_4$,$\beta$-$OR_5$,$\beta$-$R_4$" should read -- $R_2$ is H,H; =O; $\alpha$-$R_4$,$\beta$-$OR_5$; or $\alpha$-$OR_5$,$\beta$-$R_4$ --.

Column 38, line 9, "2 to carbon atoms" should read -- 2 to 5 carbon atoms --.

UNITED STATES PATENT OFFICE
CERTIFICATE OF CORRECTION

Patent No. 4,496,742          Dated January 29, 1985

Inventor(s) Herman W. Smith

It is certified that error appears in the above-identified patent and that said Letters Patent are hereby corrected as shown below:

Column 40, line 25, "10,11-didethydro-" should read -- 10,11-didehydro- --.

Signed and Sealed this

Twenty-ninth Day of July 1986

[SEAL]

Attest:

DONALD J. QUIGG

Attesting Officer      Commissioner of Patents and Trademarks